US008524693B2

(12) United States Patent
Iglesias Retuerto et al.

(10) Patent No.: US 8,524,693 B2
(45) Date of Patent: Sep. 3, 2013

(54) PROCESS FOR OBTAINING 17-SPIROLACTONES IN STEROIDS

(75) Inventors: Jesús Miguel Iglesias Retuerto, Boecillo-Valladolid (ES); Luis Gerardo Gutiérrez Fuentes, Boecillo-Valladolid (ES); Antonio Lorente Bonde-Larsen, Boecillo-Valladolid (ES)

(73) Assignee: Crystal Pharma, S.A., Boecillo-Valladolid (ES)

( * ) Notice: Subject to any disclaimer, the term of this patent is extended or adjusted under 35 U.S.C. 154(b) by 352 days.

(21) Appl. No.: 12/816,406

(22) Filed: Jun. 16, 2010

(65) Prior Publication Data
US 2011/0144363 A1 Jun. 16, 2011

(30) Foreign Application Priority Data
Jun. 16, 2009 (EP) .................... 09382096

(51) Int. Cl.
*A61K 31/58* (2006.01)
*A61K 31/585* (2006.01)
*A61K 31/56* (2006.01)
*C07J 21/00* (2006.01)
*C07J 53/00* (2006.01)

(52) U.S. Cl.
USPC ........... 514/173; 514/175; 514/178; 514/182; 540/41; 552/513

(58) Field of Classification Search
CPC .......... C07J 21/00; C07J 53/00; A61K 31/56; A61K 31/58; A61K 31/585

USPC ................ 552/513; 514/173, 178, 182, 175; 540/41
See application file for complete search history.

(56) References Cited

U.S. PATENT DOCUMENTS

| 3,687,951 | A | * | 8/1972 | Humburger et al. | ............ 544/94 |
| 4,129,564 | A | | 12/1978 | Wiechert et al. | |
| 4,345,984 | A | * | 8/1982 | Mihelich | .................. 204/157.69 |
| 4,416,985 | A | | 11/1983 | Petzoldt et al. | |
| 6,121,465 | A | | 9/2000 | Mohr et al. | |
| 7,144,551 | B2 | * | 12/2006 | Helton et al. | .................... 422/37 |
| 7,585,971 | B2 | | 9/2009 | Costantino et al. | |
| 2010/0261896 | A1 | * | 10/2010 | Nickisch et al. | ................. 540/15 |

FOREIGN PATENT DOCUMENTS

| EP | 1571153 A2 | 2/2005 |
| EP | 1746101 A1 | 7/2005 |
| WO | 2006061309 A1 | 6/2006 |

OTHER PUBLICATIONS

Bandini, Marco, et al., "A Nonclassical Stereoselective Semi-Synthesis of Drospirenone via Cross-Metathesis Reaction," Synthesis, 2008, pp. 3801-3804, No. 23.
Bittler, Dieter, et al., "Synthesis of spirorenone, a novel highly active aldosterone antagonist," Angewandte Chemie, 1982, pp. 718-719, vol. 94, No. 9.

* cited by examiner

*Primary Examiner* — Barbara P Badio
(74) *Attorney, Agent, or Firm* — Tristan A. Fuierer; Moore & Van Allen, PLLC

(57) ABSTRACT

The invention relates to processes for obtaining steroids with a spirolactone group in position 17, particularly to industrially obtaining 6β,7β; 15β,16β-dimethylene-3-oxo-17α-pregn-4-ene-21,17-carbolactone, commonly known as Drospirenone, as well as to intermediates useful in said process.

14 Claims, No Drawings

PROCESS FOR OBTAINING 17-SPIROLACTONES IN STEROIDS

CROSS REFERENCE TO RELATED APPLICATIONS

This application claims priority under 35 U.S.C. §119(a) of European Patent Application No. EP09382096.7 for "Process for Obtaining 17-Spirolactones in Steroids" filed on Jun. 16, 2009 in the name of Jesús Miguel IGLESIAS RETUERTO et al., which is incorporated herein in its entirety.

FIELD OF THE INVENTION

The invention relates to processes for obtaining steroids with a spirolactone group in position 17, particularly to industrially obtaining 6β,7β;15β,16β-dimethylene-3-oxo-17α-pregn-4-ene-21,17-carbolactone, commonly known as Drospirenone, as well as to intermediates useful in said process.

BACKGROUND OF THE INVENTION

The compounds referred to in the invention can be, for example, Drospirenone, Spirorenone or Prorerone, with particular interest in Drospirenone of formula (I):

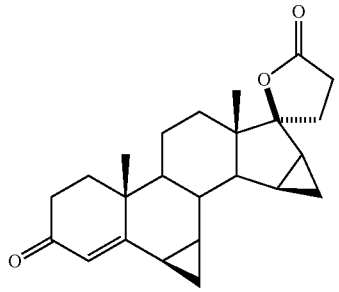

(I)

Drospirenone particularly has a progestogenic, antimineralocorticoid and antiandrogenic activity; it is therefore being used in pharmaceutical compositions for its use as a contraceptive.

Many chemical processes for obtaining it have been described, in which the main synthetic difficulties are: the arrangement of the cyclopropyl groups in the Beta configuration and the introduction of the lactone group.

DE 2 652 761, in which this compound was first described, describes a synthetic route for obtaining it in which the lactone group is introduced in early steps of the synthesis:

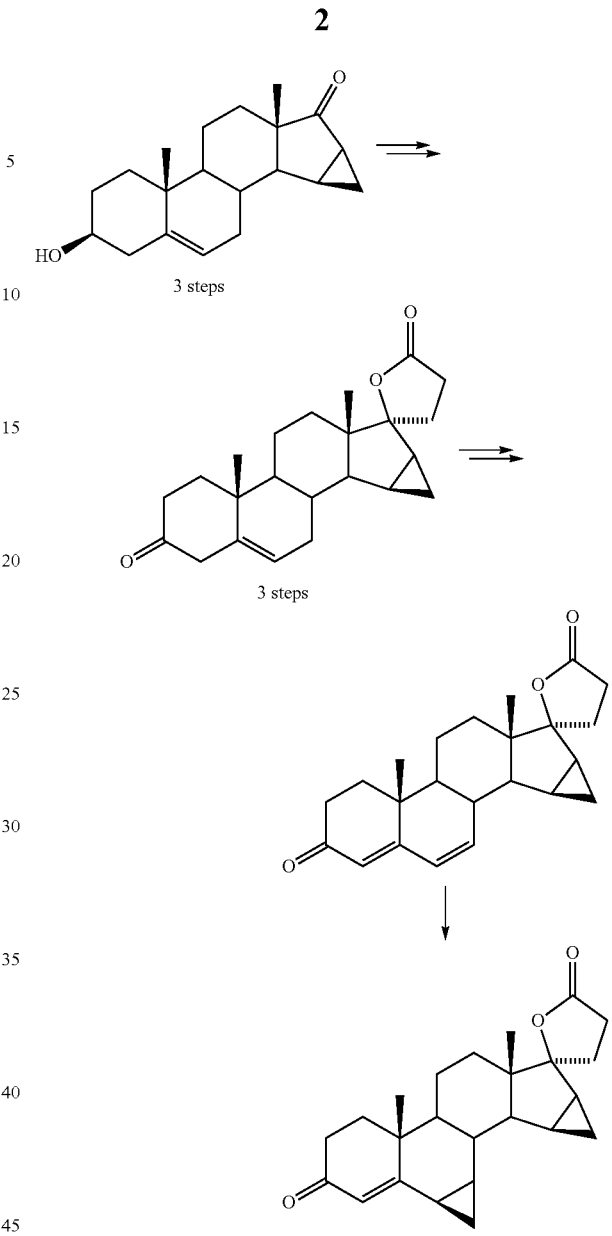

This process has the following main drawbacks: the non-diastereoselective introduction of cyclopropyl in position 6,7, which forces performing purifications by means of non-industrial techniques such as column chromatography, and the instability of the lactone group in position 17, which can be isomerized, particularly in acid medium, as has been described in Steroids, 71, 745-50, 2006 and in EP 918791 B1, giving rise to the isolactone, which is one of the main impurities associated to the end product.

In particular, to prevent the isomerization of the lactone and the appearance of the isolactone as an associated impurity which is very difficult to purify, it is desirable to use a synthesis route in which the introduction of the lactone group as a final step of the synthesis is achieved and in which furthermore the reaction conditions when it is formed are controlled.

U.S. Pat. No. 4,416,985 describes a process in which the diastereoselective introduction of cyclopropyl in position 6,7 is resolved and the lactone is obtained in the last synthesis steps:

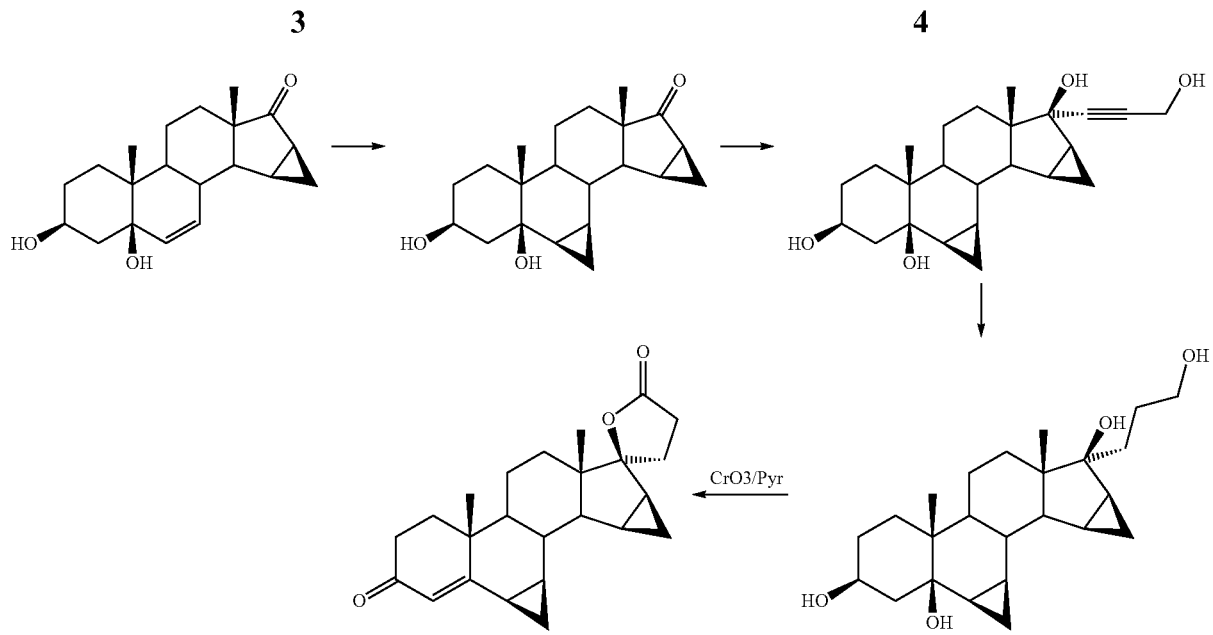

wherein the lactone is introduced simultaneously by means of adding a propargyl alcohol which is subjected to a hydrogenation and subsequent oxidation of the tetraol formed to yield the desired product.

However, the oxidation conditions of the final step, in the presence of a toxic oxidant such as $CrO_3$, give rise to a product which is purified by a chromatographic column and in which the partial isomerization of the lactone formed occurs both due to the acid medium used and due to the presence of chromium salts aiding in the isomerization.

EP 918791 B1 shows the drawbacks set forth above and proposes as a solution mitigating the final oxidation conditions of the tetraol intermediate by means of using catalytic amounts of ruthenium trichloride in the presence of sodium bromate. Under these conditions, the 5-β-hydroxy derivative:

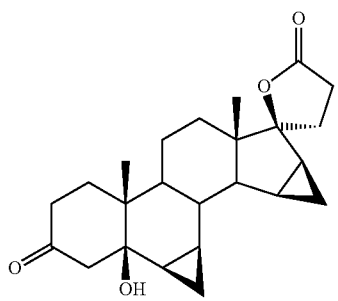

is isolated as an intermediate, which gives rise to the final Drospirenone by means of eliminating the hydroxyl group in acid medium under controlled conditions, thus preventing the appearance of the isolactone.

Under these conditions, the isolation of Drospirenone with a chromatographic purity of only 93% and the need to use chromatographic techniques if a product with a higher purity is to be obtained are described.

US 2005/192450 also uses the tetraol intermediate to, by means of its oxidation, directly obtain final Drospirenone or by previously isolating the lactol derivative:

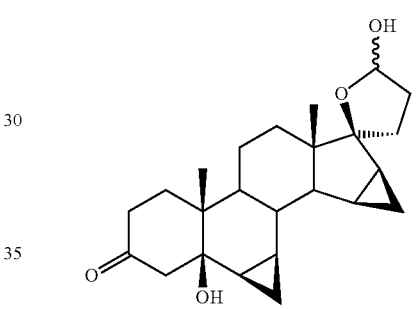

Various oxidation conditions are described, such as for example the use of $MnO_2$, Oppenauer oxidation conditions, NaClO in the presence of TEMPO etc. In this case, the Drospirenone obtained is also purified by column chromatography.

Other patents or patent applications following the same strategy of partial or complete oxidation of the tetraol intermediate under oxidizing conditions are, for example: EP 1828222 B1 and EP 1746101 B1.

As it can be seen, the strategy of all the synthetic proposals for introducing the lactone group as a final step of the synthesis is a complete or partial oxidation reaction of the tetraol intermediate, followed by elimination in acid medium to yield Drospirenone. In all the cases, the final conditions of the last step involve oxidation reagents which complicate the purification of the end product and elimination conditions in acid medium which enable the appearance of impurities derived from the degradation of the lactone, such as for example the isolactone.

It is therefore necessary to develop an alternative process for obtaining steroid derivatives with a spirolactone function which overcomes all or part of the problems associated with the known processes belonging to the state of the art.

SUMMARY OF THE INVENTION

The invention faces the problem of providing a process for preparing steroids, and particularly Drospirenone, which allows introducing the lactone group in position 17, preferably as a last synthesis step, and which prevents using oxidizing reagents complicating the final purification or acid conditions favoring the degradation of the end product, with the appearance, for example, of the isolactone.

The solution provided by the invention is based on the fact that the inventors have surprisingly observed that it is possible to introduce, in a non-oxidative manner, a lactone group, by means of introducing an alkynyl ester, particularly a propargyl ester, in position 17 of a derivative of 6β,7β;15β,16β-dimethylene-17-carbonyl steroid of formula (IV) [defined below], to give rise to a derivative of 6β,7β;15β,16β-dimethylene-17-beta-hydroxy-17-α-carboxyalkyl-ethynyl steroid of formula (III) [defined below].

A process such as the one provided by the present invention has a number of advantages since the side chain with the carboxyl group in the form of ester, necessary for subsequently creating the spirolactone, is introduced in a single synthesis step.

The present invention therefore provides an efficient process for obtaining derivatives of 6β,7β;15β,16β-dimethylene-17-hydroxy-17-carboxy-alkylethynyl steroids of formula (III), or solvates thereof, which constitute synthetic intermediates useful in the synthesis of steroids, particularly, Drospirenone.

Thus, in an aspect, the invention relates to a compound of formula (III)

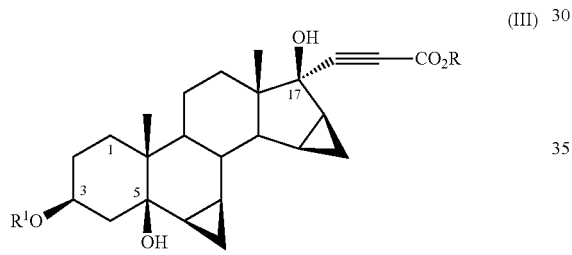

wherein
R is $C_1$-$C_8$ alkyl, $C_3$-$C_8$ cycloalkyl, aryl or benzyl; and
$R^1$ is hydrogen or a hydroxyl-protecting group;
or a solvate thereof.

In another aspect, the invention relates to a process for obtaining a compound of formula (III), which comprises reacting a compound of formula (IV)

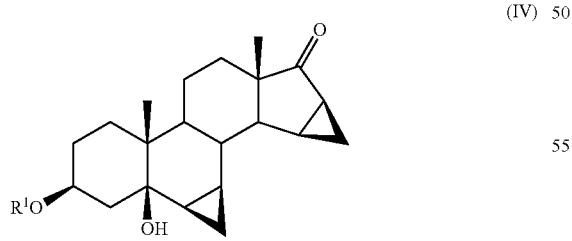

with a propargyl ester of formula (V):

  (V)

wherein R and $R^1$ are defined as above, in the presence of a base.

In another aspect, the invention relates to a process for obtaining Drospirenone (I)

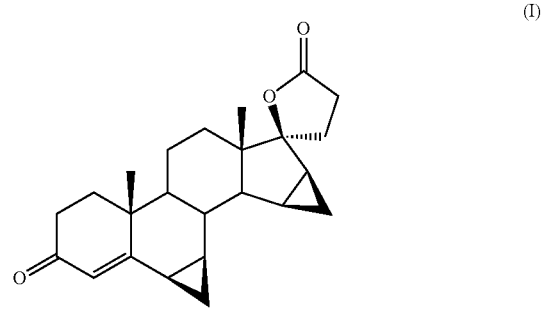 [SMILES: C[C@]12CCC(=O)C=C1[C@@H]1C[C@@H]1C1C2CC[C@@]2(C)C1[C@@H]1C[C@@H]1[C@@]21CCC(=O)O1]

which comprises providing a compound of formula (III) and subjecting said compound to:
1) optionally, deprotection of the hydroxyl in position 3 when $R^1$ is a hydroxyl-protecting group,
2) oxidation of the hydroxyl group in position 3 to yield a compound of formula (II)

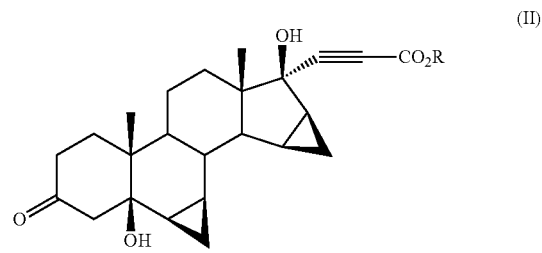

wherein R is that previously defined in connection with the compound of formula (III), and
subjecting said compound of formula (II) to a sequence of reactions selected from sequences A, B and C wherein
Sequence A comprises:
a1) subjecting a compound of formula (II) to an elimination or an elimination/saponification reaction to yield the intermediate of formula (IIa):

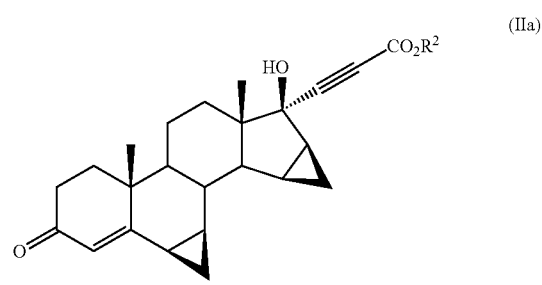

wherein $R^2$ is H, $C_1$-$C_8$ alkyl, $C_1$-$C_8$ cycloalkyl, aryl or benzyl;
a2) subjecting said compound of formula (IIa) to a hydrogenation reaction in the presence of a Pt or Pd catalyst to yield the intermediate of formula (IIc):

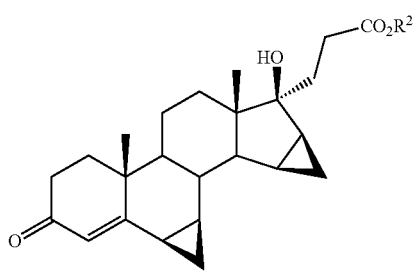

(IIc)

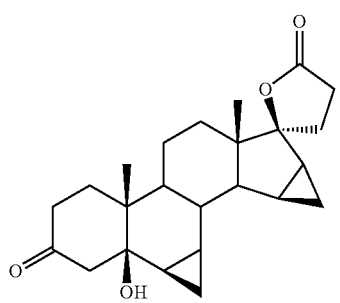

(IId)

wherein $R^2$ is that previously defined, and a3) subjecting said compound of formula (IIc) to treatment in acid conditions to render Drospirenone (I), wherein steps a2) and a3), alternatively, take place in one-pot form;

Sequence B comprises:

b1) subjecting a compound of formula (II) to a hydrogenation reaction in the presence of a Pd catalyst to yield the intermediate of formula (IIb)

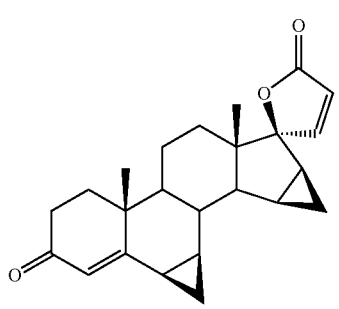

(IIb)

and b2) subjecting said compound of formula (IIb) to a hydrogenation reaction in the presence of a Pt catalyst to render Drospirenone (I);

wherein steps b1) and b2) alternatively take place in one-pot form; and

Sequence C comprises:

c1) subjecting a compound of formula (II) to a hydrogenation reaction in the presence of a Pt catalyst to yield the intermediates of formulae (IId) and/or (IIe)

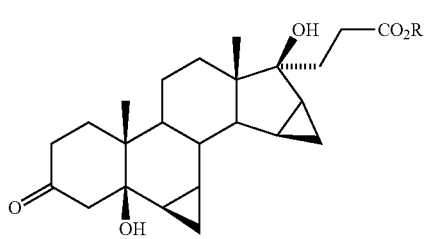

(IIe)

wherein R is that previously defined, and c2) subjecting a compound of formulae (IId) and/or (IIe) to treatment in acid conditions to render Drospirenone (I), wherein steps c1) and c2) alternatively take place in one-pot form.

In another aspect, the invention is aimed at a process for obtaining Drospirenone (I):

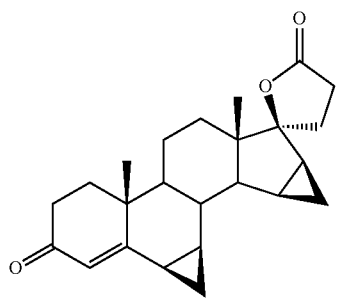

(I)

comprising providing a compound of formula (III) as defined above, followed by d1) subjecting said compound of formula (III) to a hydrogenation reaction in the presence of a metal catalyst to yield the intermediate of formula (VI)

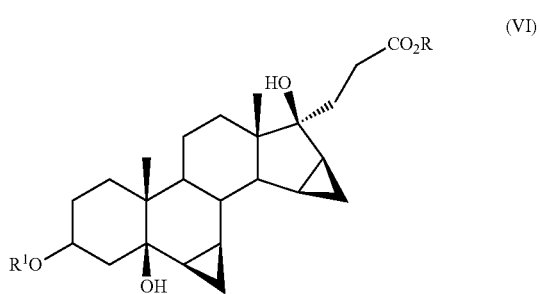

(VI)

wherein R is that previously defined, d2) deprotecting the hydroxyl group in position 3 of said compound of formula (VI) when $R^1$ is a protecting group, followed by a transesterification reaction to render the compound of formula (VII)

(VII)

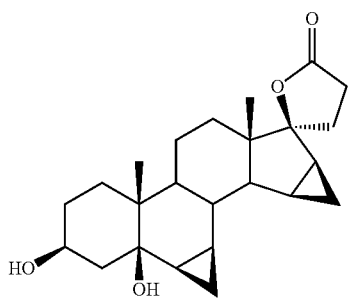

d3) oxidizing the compound of formula (VII) to render the compound of formula (IId)

(IId)

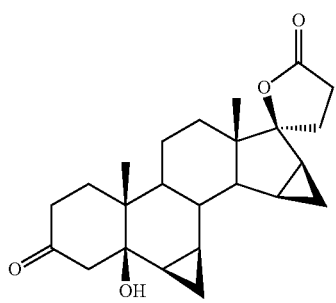

and d4) subjecting the compound of formula (IId) to an elimination reaction to render Drospirenone (I).

In another aspect, the invention relates to a compound selected from the following list:

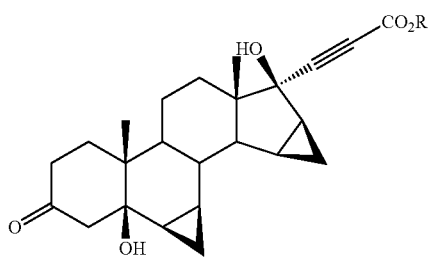

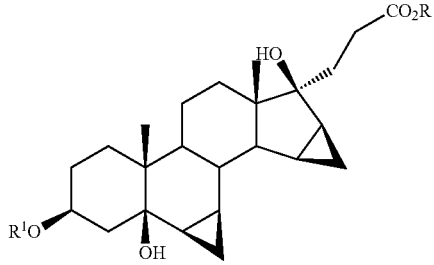

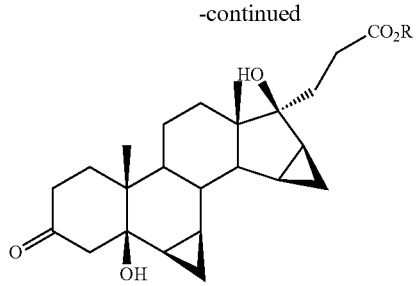

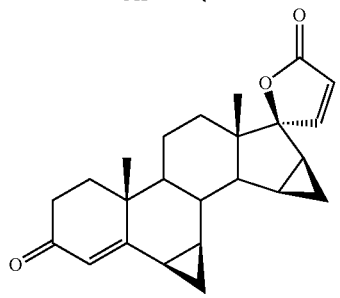

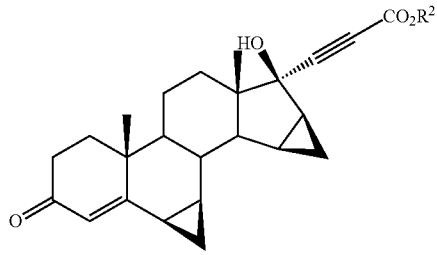

or a solvate thereof, wherein R, $R^1$ and $R^2$ are as they have been defined above.

DETAILED DESCRIPTION OF THE INVENTION

In the context of the present invention, the following terms have the meaning detailed below:

The term "$C_1$-$C_8$ alkyl" refers to a radical derived from a linear or branched alkane, containing from 1 to 8, preferably from 1 to 6 carbon atoms ("$C_1$-$C_6$ alkyl"), and which is attached to the rest of the molecule by a single bond. Examples of alkyl groups include methyl, ethyl, propyl, butyl, pentyl and hexyl.

As used herein, the term "$C_3$-$C_8$ cycloalkyl" refers to a radical derived from a cycloalkane, containing from 3 to 8, preferably from 3 to 6 ("$C_3$-$C_6$ cycloalkyl") carbon atoms. Examples of cycloalkyl groups include cyclopropyl and cyclobutyl.

As defined herein, the term "aryl" refers to a radical derived from an aromatic hydrocarbon containing from 6 to 14, preferably from 6 to 10 carbon atoms, for example, phenyl, tolyl, xylyl, naphthyl, etc.

As used herein, the term "hydroxyl-protecting group" includes any group capable of protecting a hydroxyl group. Illustrative examples of said hydroxyl-protecting groups have been described by Green T. W. et al. in "Protective Groups in Organic Synthesis", 3rd Edition (1999), Ed. John Wiley & Sons. Examples of hydroxyl-protecting groups include silyl ethers, ethers, esters, sulfonates, sulfenates, sulfinates, carbonates and carbamates. The hydroxyl-protecting group is preferably a silyl radical of formula $Si(R^6)(R^7)(R^8)$, wherein $R^6$, $R^7$, $R^8$ represent, independently from one another, $C_1$-$C_6$ alkyl or $C_3$-$C_6$ cycloalkyl.

Likewise, the compounds described in the present invention can be in crystalline form, either as free compounds or as solvates (for example, hydrates) and it is understood that both forms are within the scope of the present invention. Solvation methods are generally known in the art. Suitable solvates are pharmaceutically acceptable solvates.

Compound of Formula (III)

In an aspect, the invention relates to a compound of formula (III)

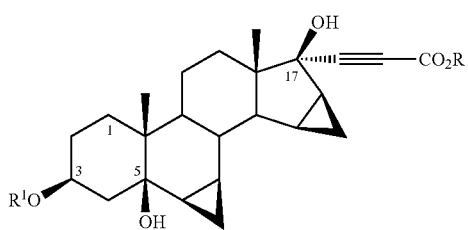

wherein

R is $C_1$-$C_8$ alkyl, $C_3$-$C_8$ cycloalkyl, aryl or benzyl; and $R^1$ is hydrogen or a hydroxyl-protecting group;

or a solvate thereof.

In a particular embodiment, R is $C_1$-$C_8$ alkyl, preferably $C_1$-$C_3$ alkyl, more preferably ethyl.

In another particular embodiment, $R^1$ is selected from hydrogen and a silylated hydroxyl-protecting group. Preferably, $R^1$ is selected from hydrogen, trimethylsilyl and tert-butyldimethylsilyl.

In another particular embodiment, R is linear or branched $C_1$-$C_3$ alkyl and $R^1$ is selected from hydrogen and a silylated hydroxyl-protecting group. In another more particular embodiment, R is ethyl and $R^1$ is preferably selected from hydrogen, trimethylsilyl and tert-butyldimethylsilyl.

According to a particular embodiment, the compound of formula (III) is selected from:

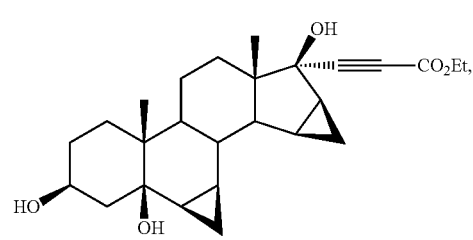

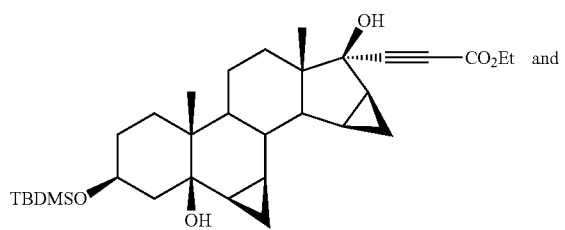

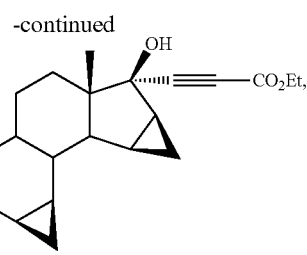

or a solvate thereof.

Process for Obtaining a Compound of Formula (III)

In another aspect, the invention relates to a process, hereinafter referred to as the "process of the invention", for obtaining a compound of formula (III)

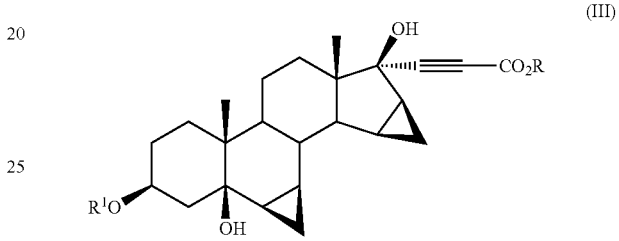

wherein

R is $C_1$-$C_8$ alkyl, $C_3$-$C_8$ cycloalkyl, aryl or benzyl; and $R^1$ is hydrogen or a hydroxyl-protecting group;

or a solvate thereof, which comprises reacting a compound of formula (IV)

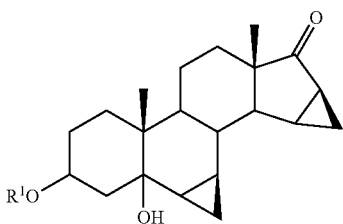

wherein $R^1$ is that previously defined, with a propargyl ester of formula (V)

$$RO_2C\equiv H \qquad (V)$$

wherein R is that previously defined, in the presence of a base.

The process of the invention comprises reacting the compound of formula (IV) with an anion of the propargyl ester which is generated by means of the reaction of a base with a propargyl ester (V).

To put the process of the invention into practice, various propargyl esters can be used, particularly of the group consisting of ethyl propiolate, methyl propiolate, tert-butyl propiolate, isobutyl propiolate, and mixtures thereof. In a particular and preferred embodiment, the propargyl ester is ethyl propiolate.

The base used in the process of the invention can be any organic or inorganic base capable of abstracting the proton of a propargyl ester. Illustrative non-limiting examples of organic or inorganic bases which can be used include amides such as lithium diethylamide, lithium diisopropylamide (LDA), lithium hexamethyldisilazide (HMDSLi), lithium amide, sodium amide, etc., lithium alkylides such as butyllithium, hexyllithium, etc.; sodium hydride, lithium hydride, or any other similar inorganic base which is considered capable of abstracting the proton of propargyl esters. One or more organic and/or inorganic bases can be used. In a particular embodiment of the invention, the organic base is selected from lithium diethylamide, HMDSLi (lithium hexamethyldisilazide), LDA (lithium diisopropylamide) and mixtures thereof, and the inorganic base is selected from lithium amide, sodium amide and mixtures thereof. More preferably the base is lithium amide.

In a particular embodiment, the reaction of the compound of formula (IV) with the propargyl ester (V) is carried out in a suitable organic solvent, such as an ether, for example, an acyclic ether (e.g., diisopropylether, etc.) or a cyclic ether (e.g., tetrahydrofuran (THF), a dioxane, etc.), a halogenated solvent such as, for example, dichloromethane, etc., or in an aromatic solvent such as, for example, toluene, etc.

The addition reaction of the process of the invention is preferably carried out in the presence of an excess of base. For example, when lithium amide in toluene is used, the use of between 2 and 20 equivalents of base against 1 equivalent of the steroid of formula (IV), preferably between 4 and 14 equivalents of base, is required.

The amount of propargyl ester (V) can also vary within a broad range, typically between 1 and 6 equivalents, preferably between 1.2 and 2 equivalents, with respect to the steroid of formula (IV).

Although the background documents found indicate, for example, that the lithium anions obtained from propargyl esters readily decompose at temperatures greater than −78° C., (see for example: *J. Org. Chem.*, 45, 28, 1980; *J. Am. Chem. Soc.*, 122, 10033, 2000; *Fieser and Fieser's Reagents for Organic Synthesis*, vol 8, p. 259, Wiley Interscience and *Synthesis*, 679, 1977), the inventors have surprisingly found that both the formation of the anion of the propargyl ester with a base and its subsequent addition to the steroid can be performed at higher temperatures without this involving the decomposition of any particular compound. Therefore, in a particular embodiment, the temperature at which the process of the invention is performed ranges between −10° C. and 60° C., not being necessary to perform the reaction in the drastic cooling conditions described in the prior art of typically −76° C. The process of the invention surprisingly overcomes the drawbacks set forth in the prior art (see *J. Am. Chem. Soc.*, 83, 2944, 1961), which describes the formation of trimers and other derivatives of propargyl esters upon reacting with catalysts at room temperature or above.

The reaction rate depends on both the temperature and the solvent used, where at a temperature comprised between −10° C. and 60° C. the reaction takes place in a time period of between 15 minutes and 12 hours, typically comprised between 30 minutes and 6 hours.

In a particular embodiment, when the reaction is carried out using tetrahydrofuran as a solvent and lithium amide as a base, the typical reaction temperature is comprised between 0° C. and 5° C. and the reaction time is approximately 2-3 hours.

According to another particular embodiment, when using tetrahydrofuran/dimethylformamide (THF/DMF) mixtures as the solvent and sodium amide as the base, the typical reaction temperature is between 0° C. and 5° C. and the reaction time is approximately 3-4 hours.

According to another particular embodiment, when using toluene as the solvent and lithium amide as the base, the reaction temperature is about 25° C. and the reaction time is approximately 2-4 hours.

According to another particular embodiment, when using toluene as the solvent and lithium amide as the base, the reaction temperature is about 40° C. and the reaction time is approximately 1-3 hours.

According to another particular embodiment, when using toluene as the solvent and HMDSLi as the base, the reaction temperature is about 0° C. and the reaction time is approximately 0.5-3 hours.

In any of these cases, a significant increase in the reaction temperature can involve an increase of impurities, mainly derived from the polymerization of the propargyl ester and also a reduction in the final yield.

The process of the invention allows obtaining compounds of formula (III) with a high degree of purity and with high yields, typically of approximately 80%, or higher.

The compounds of formula (III) obtained can be used directly or can be purified by means of conventional and industrially acceptable processes such as, for example, by means of a crystallization process. Illustrative non-limiting examples of suitable solvents for said crystallization include ethyl acetate, toluene, heptane, methyl tert-butyl ether, dichloromethane (DCM), etc., and mixtures thereof. In a preferred embodiment, said solvent is selected from ethyl acetate, toluene, dichloromethane, heptane and mixtures thereof.

In a particular embodiment, when, in the compound of formula (III), R is ethyl and $R^1$ is a tert-butyldimethylsilyl (TBDMS) group, the product can be purified in toluene or toluene/heptane to yield the corresponding toluene hemisolvate.

According to another particular embodiment, when, in the compound of formula (III), R is ethyl and $R^1$ is hydrogen, the product can be purified in DCM or DCM/heptane.

According to a particular embodiment, the formation reaction of a compound of formula (III) is performed by means of the reaction of a compound of formula (IV) wherein $R^1$ is a TBDMS group and a compound of formula (V) wherein R is an ethyl group, using 8 equivalents of lithium amide in toluene, giving rise to the corresponding compound of formula (III) which is isolated in the form of toluene hemisolvate with a yield greater than 80%.

According to another particular embodiment, the formation reaction of a compound of formula (III) is performed by means of the reaction of a compound of formula (IV) wherein $R^1$ is a TBDMS group and a compound of formula (V) wherein R is an ethyl group, using 2 equivalents of HMDSLi in toluene, giving rise to the corresponding compound of formula (III) which is isolated in a yield of about 77%.

The starting products of formula (IV), wherein $R_1$ is H, can be obtained by methods known in the state of the art as mentioned, for example, in U.S. Pat. No. 4,416,985, U.S. Pat. No. 4,435,327 or in EP 1828222, which describe obtaining keto derivatives in position 17 according to the following synthetic scheme:

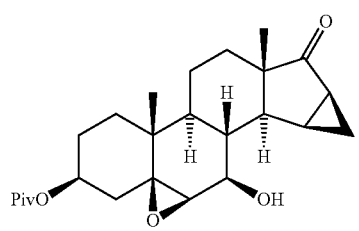 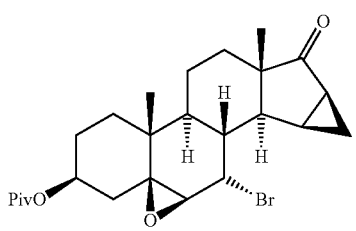 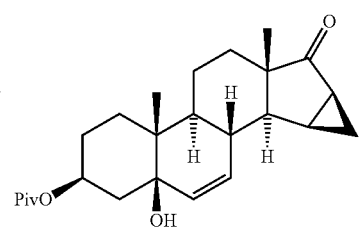

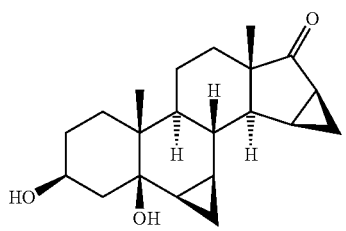

The compounds of formula (IV) wherein $R^1$ is a hydroxyl-protecting group can in turn be obtained from the compound of formula (IV) wherein $R^1$ is H, by means of protecting the hydroxyl group by methods known in the state of the art for the protection of hydroxyl groups, such as, for example, by means of those described by Green T. W. et al. in "Protective Groups in Organic Synthesis", 3rd Edition (1999), Ed. John Wiley & Sons (ISBN 0-471-16019-9).

In a particular embodiment, the compounds of formula (IV) wherein $R^1$ is a TBDMS group or a TMS (trimethylsilyl) group are obtained by means of the reaction of the compound (IV) wherein $R^1$ is H with tert-butyldimethylsilyl chloride or with trimethylsilyl chloride, respectively, in DMF and in the presence of a base such as, for example, triethylamine. These compounds can be crystallized in DMF/water.

In another aspect, the invention relates to the use of said steroids of formula (III) or solvates thereof, as intermediates useful in the synthesis of steroids with a spirolactone group in position 17, preferably in the synthesis of Drospirenone (I).

Process for Obtaining Drospirenone (I)

Another aspect of the present invention relates to a process for obtaining Drospirenone (I)

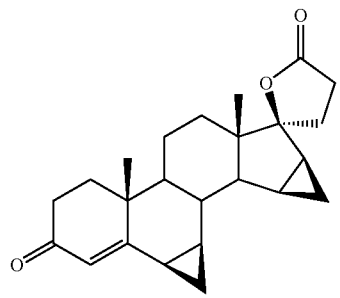

(I)

which comprises
providing a compound of formula (III)

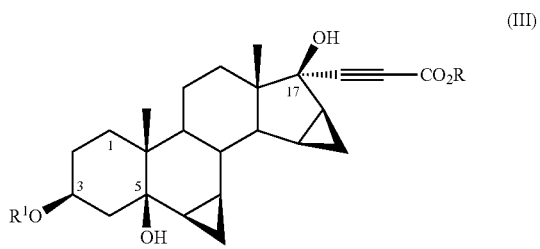

(III)

wherein
R is selected from $C_1$-$C_8$ alkyl, $C_3$-$C_8$ cycloalkyl, aryl and benzyl; and
$R^1$ is selected from hydrogen and a hydroxyl-protecting group;
or a solvate thereof, and
subjecting said compound of formula (III) to:
1) optionally, deprotection of the hydroxyl group in position 3 when $R^1$ is a protecting group, and
2) oxidation of the hydroxyl group in position 3 to render a compound of formula (II)

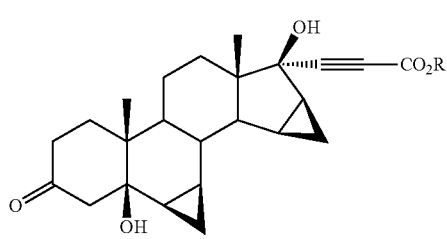

(II)

wherein R is that previously defined, and
subjecting said compound of formula (II) to a sequence of reactions selected from sequences A, B and C (below).
In a particular embodiment, R is linear or branched $C_1$-$C_8$ alkyl, preferably $C_1$-$C_3$ alkyl, more preferably ethyl.
In another particular embodiment, $R^1$ is hydrogen or a silylated hydroxyl-protecting group, preferably, in a more particular embodiment, $R^1$ is hydrogen, trimethyl-silyl or tert-butyldimethylsilyl.

In another particular embodiment, R is linear or branched $C_1$-$C_3$ alkyl and $R^1$ is hydrogen or a silylated hydroxyl-protecting group. Preferably, in a more particular embodiment, R is ethyl and $R^1$ is hydrogen, trimethylsilyl or tert-butyldimethylsilyl.

Particular embodiments of the invention include the use of compounds of formula (III) in which:

R is ethyl and $R^1$ is hydrogen;

R is ethyl and $R^1$ is tert-butyldimethylsilyl; or

R is ethyl and $R^1$ is trimethylsilyl.

If necessary, the hydroxyl group deprotection reaction 1) can be carried out by conventional methods, for example, according to any of the methods described by Green T W et al. in "Protective Groups in Organic Synthesis", $3^{rd}$ Edition (1999), Ed. John Wiley & Sons (ISBN 0-471-16019-9). It will depend, among other things, on the nature of the hydroxyl-protecting group.

When the protecting group $R^1$ in the compound of formula (III) is a silyl group, it can be readily eliminated using for example fluoride salts, inorganic acids such as hydrochloric acid in ethanol, organic acids such as formic acid in tetrahydrofuran or para-toluenesulfonic acid and in some occasions, oxidative media such as 2,3-dichloro-5,6-dicyanobenzoquinone (DDQ).

Particularly, when said protecting group $R^1$ is trimethylsilyl (TMS) or tert-butyldimethylsilyl (TBDMS), fluoride salts such as pyridinium fluoride, potassium fluoride or ammonium fluoride can be used for its elimination. Tetrabutylammonium fluoride in a solvent such as tetrahydrofuran and at room temperature is more preferably used, the yields obtained being quantitative or almost quantitative.

The compounds of formula (III) obtained after step 1) can be used directly or can be purified by means of conventional and industrially acceptable processes such as, for example, by means of a crystallization process. Illustrative non-limiting examples of suitable solvents for said crystallization include dichloromethane, heptane, toluene, methyl tert-butyl ether and mixtures thereof. In a preferred embodiment, said solvent is selected from dichloromethane and dichloromethane/heptane. In a particular embodiment, when R is an ethyl group, the compound of formula (III) can be crystallized in dichloromethane and dichloromethane/heptane.

Alternatively, when the protecting group $R^1$ in the compound of formula (III) is an ether derivative such as, for example, methoxymethyl ether, tetrahydropyranyl ether, or 2-methoxy-ethoxymethyl ether, they can be eliminated by using acid media.

When the protecting group $R^1$ in the compound of formula (III) is an ester derivative such as, for example, a phenyl ester, it can be eliminated by using fluoride salts such as tetrabutylammonium fluoride or methanolic sodium hydroxide.

When the protecting group $R^1$ in the compound of formula (III) is a trihaloacetate, particularly trifluoroacetate, it can be eliminated in mild basic conditions.

The compound of formula (III) wherein $R^1$ is H can be converted into the intermediate of formula (II) by means of an oxidation reaction (step 2):

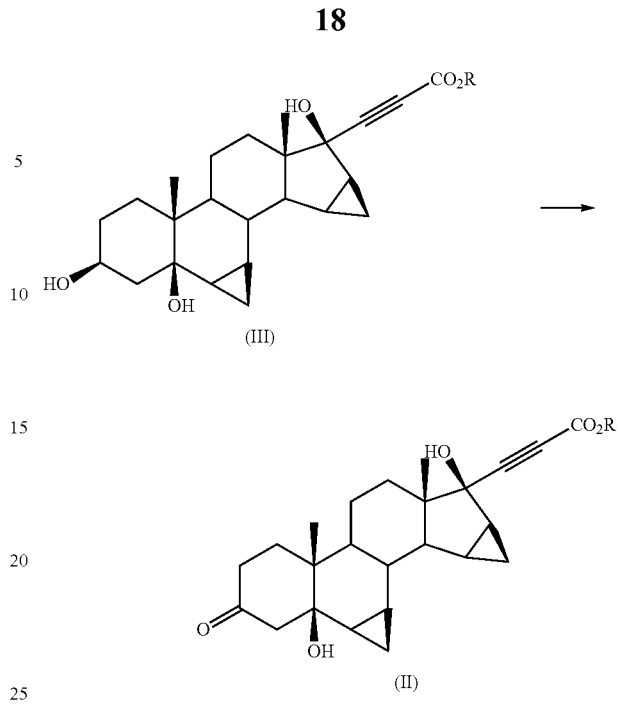

wherein R is that previously defined.

This step can be carried out by means of any oxidation reaction which allows transforming a hydroxyl group into a carbonyl group, following for example the processes described in U.S. Pat. No. 4,416,985, U.S. Pat. No. 6,121,465, EP 1571153 or EP 1828222, by means of using reagents such as 2,2,6,6-tetramethylpiperidine-1-oxide (TEMPO), calcium hypochlorite, trichloroisocyanuric acid or mixtures thereof.

In a particular embodiment, the transformation of a compound of formula (III) wherein R is ethyl into the corresponding ketone of formula (II) is performed through the use of trichloroisocyanuric acid in the presence of TEMPO in a two-phase system formed by a dichloromethane/tetrahydrofuran and water/sodium or potassium bicarbonate mixture at room temperature.

The compounds of formula (II) so obtained can be used directly or can be purified by means of conventional and industrially acceptable processes such as, for example, by means of a crystallization process. Illustrative non-limiting examples of suitable solvents for said crystallization include dichloromethane, heptane, toluene, methyl tert-butyl ether and mixtures thereof. In a preferred embodiment, said solvent is selected from dichloromethane, toluene and mixtures thereof with heptane. According to a particular embodiment, when R is an ethyl group, the compound of formula (II) can be purified by means of crystallization in dichloromethane (DCM), toluene, DCM/heptane or toluene/heptane.

The compound of formula (II) obtained can subsequently be transformed into Drospirenone (I) by means of a sequence of reactions selected from sequences A, B and C which are detailed below.

Sequence A comprises:

a1) subjecting a compound of formula (II) to an elimination or an elimination/saponification reaction to yield the intermediate of formula (IIa):

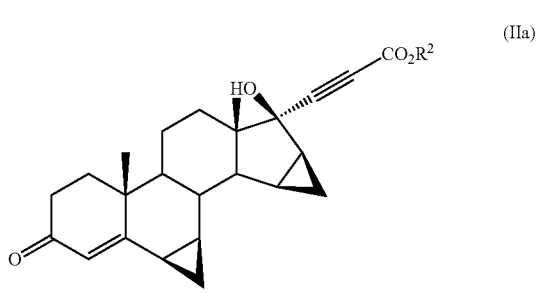

(IIa)

wherein $R^2$ is H, $C_1$-$C_8$ alkyl, $C_1$-$C_8$ cycloalkyl, aryl or benzyl;

a2) subjecting said compound of formula (IIa) to a hydrogenation reaction in the presence of a Pt or Pd catalyst to yield the intermediate of formula (IIc):

(IIc)

wherein $R^2$ is that previously defined, and a3) subjecting said compound of formula (IIc) to treatment in acid conditions to render Drospirenone (I), wherein steps a2) and a3), alternatively, take place in one-pot form.

According to the invention, the first elimination reaction [step a1)] can take place in:

a) an acid medium, comprising organic or inorganic acids, such as, for example, p-toluenesulfonic acid or potassium bisulfate in catalytic or equimolecular amounts and in a solvent, such as, for example, THF, ethyl acetate, ethanol or dichloromethane; under these conditions, the reaction preferably takes places at room temperature (about 18° C.-25° C.), or in b) a basic medium, comprising, for example, sodium carbonate, sodium hydroxide, lithium hydroxide, etc., in amounts from 1 to 3 equivalents, in a solvent such as THF, methyl-THF, acetonitrile, methanol, isopropanol, toluene or water; under these conditions the reaction can take place at a temperature from 0° C. to room temperature.

At the first stage of step a1), elimination of the hydroxyl at C5 position occurs to afford the intermediate of formula (IIa), which may be an acid ($R^2$=H) or an ester ($R^2$=$C_1$-$C_8$ alkyl, $C_1$-$C_8$ cycloalkyl, aryl or benzyl).

Saponification of the ester (IIa), as a second stage, to render the acid intermediate of formula (IIi) takes place when the reaction is performed with a basic medium and be kept under stirring, wherein $R^2$ is hydrogen, as shown below:

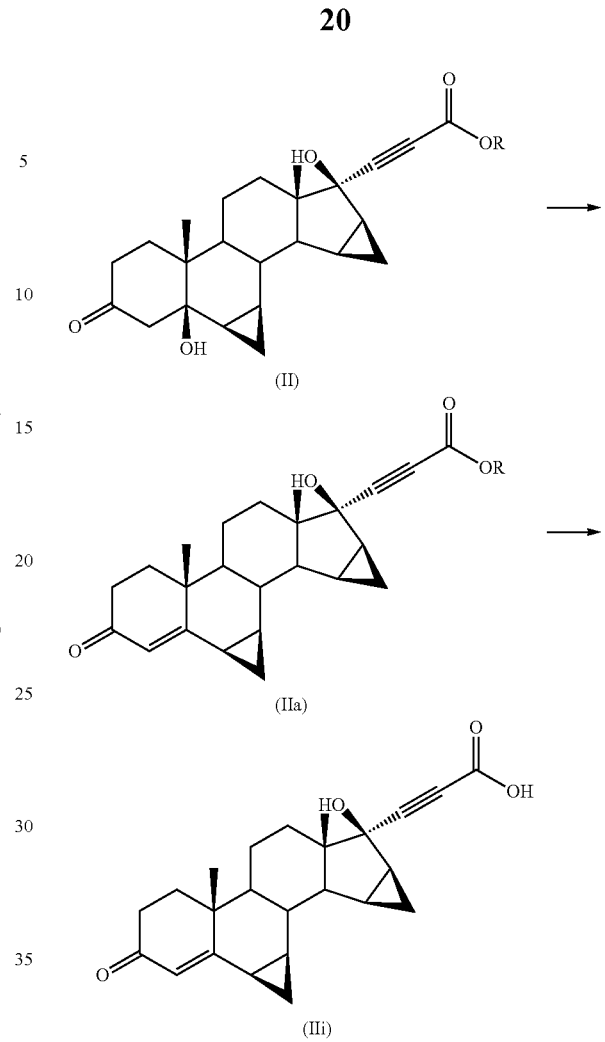

In a particular embodiment, when $R^2$ is an ethyl group, the elimination reaction a1) is carried out:
- in tetrahydrofuran using potassium bisulfate or para-toluenesulfonic acid at room temperature, to render the ester (IIa), or
- in water using lithium hydroxide at room temperature, to render the acid (III), or
- in methanol using sodium carbonate at 0° C., to render the ester (IIa).

If desired, the intermediate of formula (IIa), obtained in step a1), can be used directly in the hydrogenation step a2) or, alternatively, it can be isolated and purified by recrystallization or precipitation, using solvents such as toluene, ethyl acetate and mixtures thereof with heptane.

The hydrogenation reaction [step a2)] is performed by using Pt or Pd as a catalyst at atmospheric pressure and in the presence of solvents such as ethanol or ethyl acetate, and preferably at room temperature, to render the compound of formula (IIc).

In the hydrogenation reaction, it is possible to directly obtain Drospirenone (I) or also a mixture of Drospirenone (I) with the non-lactonized intermediate (IIc), wherein the latter, either spontaneously or with subsequent treatment in acid medium according to step a3, can be transformed into Drospirenone (I). The acid conditions in step a3) can be established by using both organic and inorganic acids such as, for example, para-toluenesulfonic acid or potassium bisulfate, typically in catalytic amounts; the reaction can take place at room temperature.

Steps a2) and a3) can alternatively take place in one-pot form by means of an acid treatment comprising the addition to the compound of formula (IIa) of an organic or inorganic acid, preferably in a catalytic manner, in a solvent such as, for example, tetrahydrofuran, ethyl acetate or ethanol, followed by the addition of a catalyst such as Pt/C or Pd/C under hydrogenation conditions at atmospheric pressure.

Sequence B comprises:
b1) subjecting a compound of formula (II) to a hydrogenation reaction in the presence of a Pd catalyst to yield the intermediate of formula (IIb)

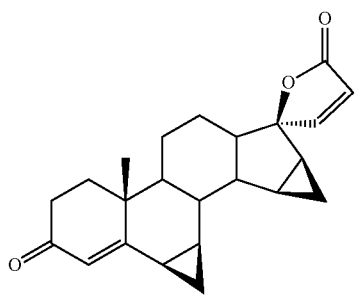

(IIb)

and
b2) subjecting said compound of formula (IIb) to a hydrogenation reaction in the presence of a Pt catalyst to render Drospirenone (I);
wherein steps b1) and b2) alternatively take place in one-pot form.

According to sequence B, the compounds of formula (II) can directly give rise to Drospirenone (I) by means of a catalytic hydrogenation process depending on the type of catalyst chosen.

Thus, when a compound of formula (II) is first subjected to hydrogenation conditions in the presence of a Pd catalyst, preferably Pd/C, followed by a second step in which a Pt catalyst, preferably Pt/C, is added, both performed at atmospheric pressure, Drospirenone (I) is directly obtained.

In a particular embodiment, this process can be performed in the form of a one-pot process, in which first a Pd catalyst and then a Pt catalyst are added.

Alternatively, the intermediate (IIb) obtained as an intermediate during the hydrogenation with Pd can be initially isolated, for example by means of filtration, and it can subsequently be transformed into Drospirenone (I) in the presence of a Pt catalyst, the same solvent or another different one being able to be used in both steps.

The intermediate (IIb) can optionally be isolated and purified, if necessary, using for example DMF/water, and can subsequently be subjected to catalytic hydrogenation in the presence of Pt/C to give rise to Drospirenone (I).

In a particular embodiment, when the hydrogenation reaction of the compound of formula (II) is performed with Pd/C at atmospheric pressure in a solvent such as ethyl acetate or ethanol, there is an elimination of the hydroxyl group in position 5 and a partial reduction of the alkyne to yield the corresponding alkene derivative which, by means of an intramolecular transesterification process, gives rise to the unsaturated lactone (IIb). Under these reaction conditions, the subsequent addition of a Pt catalyst is required to be able to reduce the unsaturated lactone (IIb) to the saturated lactone (I) or Drospirenone.

Under these conditions, both oxidative and acid conditions are avoided while obtaining Drospirenone (I).

Sequence C comprises:
c1) subjecting a compound of formula (II) to a hydrogenation reaction in the presence of a Pt catalyst to yield the intermediates of formulae (IId) and/or (IIe)

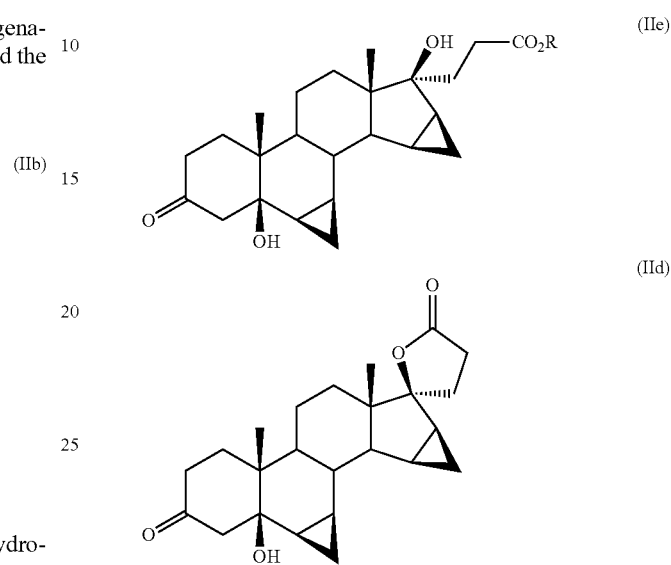

wherein R is that previously defined, and
c2) subjecting a compound of formulae (IId) and/or (IIe) to treatment in acid conditions to render Drospirenone (I);
wherein steps c1) and c2) alternatively take place in one-pot form.

In a particular embodiment, these two steps [c1) and c2)] can be performed in a one-pot process, without eliminating the catalyst.

Alternatively, sequence C can be performed in two steps, wherein once the hydrogenation has taken place, the reaction mixture is subjected to filtration to recover the catalyst, followed by an acid treatment to give rise to Drospirenone (I).

The hydrogenation reaction [step c1)] is preferably carried out using Pt/C as a catalyst at atmospheric pressure and using solvents such as ethanol or ethyl acetate. This step c1 is preferably performed at room temperature.

During the hydrogenation reaction [step c1)], the reduction of the propargyl ester to yield the intermediate of formula (IIe) and the partial transesterification of the latter to obtain the lactone of formula (IId) are observed. Both intermediates are present at the end of the hydrogenation process in a variable ratio.

The mixture of both intermediates is subjected to treatment under acid conditions [step c2)] for their transformation into Drospirenone (I) by means of the elimination of the hydroxyl group in the case of the intermediate of formula (IId) and by means of the elimination of the hydroxyl group and intramolecular transesterification to yield the lactone in the case of the intermediate of formula (IIe).

To establish the acid conditions, both organic and inorganic acids, such as for example para-toluenesulfonic acid or potassium bisulfate, in catalytic or equimolecular amounts, can be used; solvents such as tetrahydrofuran, ethyl acetate, ethanol or dichloromethane can be used; and the reaction preferably takes place at room temperature.

In a preferred embodiment, the invention provides a process for obtaining Drospirenone (I) which comprises a) protecting a compound of formula (IVa)

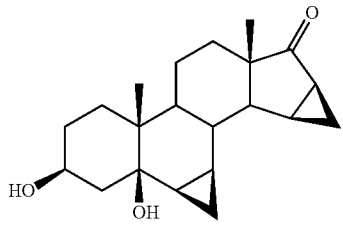
(IVa)

to render a compound of formula (IVb)

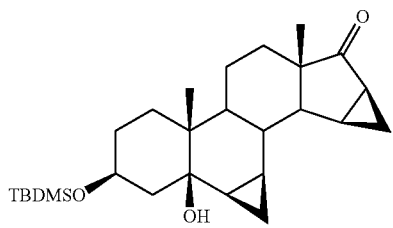
(IVb)

wherein TBDMS is tert-butyldimethylsilyl;

b) reacting said compound of formula (IVb) with a compound of formula (Va)

$H\equiv CO_2Et$ (Va)

to render a compound of formula (IIIb)

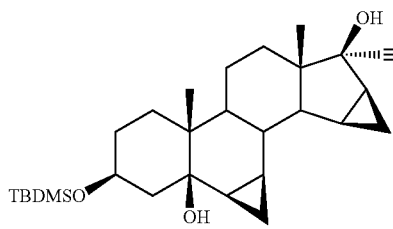
(IIIb)

wherein TBDMS is tert-butyldimethylsilyl;

c) deprotecting the protected hydroxyl group in position 3 of said compound of formula (IIIb) to render a compound of formula (IIIc)

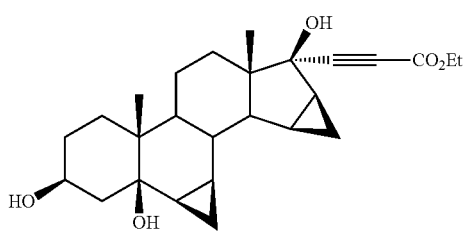
(IIIc)

d) oxidizing the hydroxyl group in position 3 of said compound of formula (IIIc) in the presence of an oxidizing species to yield a compound of formula (IIf)

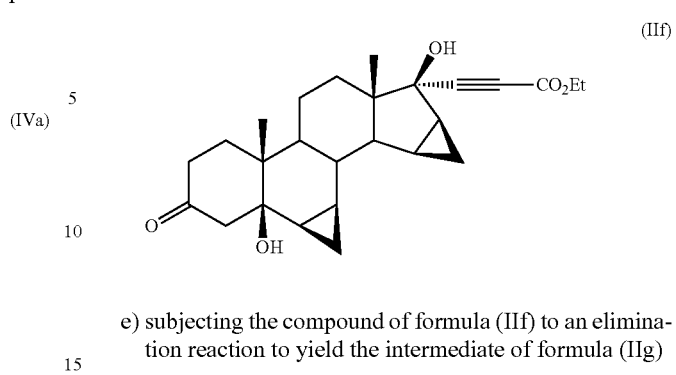
(IIf)

e) subjecting the compound of formula (IIf) to an elimination reaction to yield the intermediate of formula (IIg)

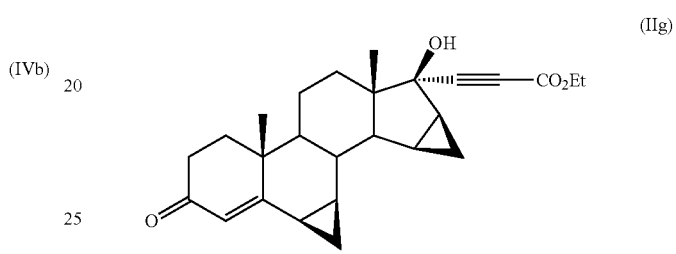
(IIg)

f) subjecting the compound of formula (IIg) to a hydrogenation reaction in the presence of a Pt catalyst to yield the intermediate of formula (IIh)

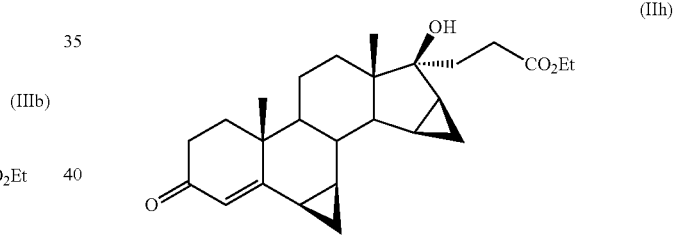
(IIh)

and g) subjecting the compound of formula (IIh) to treatment in the presence of an acid to render Drospirenone (I).

According to the invention, in a particular embodiment, the protection reaction of step a) is carried out using a TBDMS triflate or halide in the presence of a base and an organic solvent. In a preferred embodiment, the base is an organic base, preferably an amine, and the solvent is a suitable organic solvent such as an ether, a halogenated solvent or DMF. In a more particular embodiment, the reaction takes place in the presence of TBDMS chloride using triethylamine as the base and DMF as the solvent.

The reaction conditions for step b) are the same as those mentioned above in relation to the process of the invention [i.e., the process for obtaining a compound of formula (III) by reacting a compound of formula (IV) with a propargyl ester of formula (V)]. In a particular embodiment, the reaction is carried out in the presence of lithium amide or HMDSLi as a base and an aromatic solvent, preferably toluene.

Step c can be carried out using fluoride salts such as pyridinium fluoride, potassium fluoride, ammonium fluoride or tetrabutylammonium fluoride. In a particular embodiment, the reaction is carried out using tetrabutylammonium fluoride in a solvent, e.g., an ether, preferably tetrahydrofuran.

The oxidation of the hydroxyl group [step d)] is preferably carried out in the presence of an oxidizing reagent such as TEMPO, calcium hypochlorite, trichloroisocyanuric acid or mixtures thereof. In a particular embodiment, the reaction is carried out using trichloroisocyanuric acid in the presence of TEMPO and a two-phase system formed by a mixture of dichloromethane/tetrahydrofuran and water/sodium bicarbonate.

The dehydration step [step e)] preferably takes place in acid medium such as, for example, para-toluenesulfonic acid or potassium bisulfite in the presence of an organic solvent such as, for example, tetrahydrofuran, ethyl acetate, ethanol or dichloromethane. In a particular embodiment, the reaction is carried out using para-toluenesulfonic acid in a medium comprising tetrahydrofuran.

In a particular embodiment, the hydrogenation reaction [step f)] is performed using Pt/C as a catalyst in a hydrogen atmosphere, preferably at an overpressure, e.g., an overpressure of 0.1 bar ($10^4$ Pa), and in the presence of ethyl acetate.

Finally, treatment of the compound of formula (IIh) to render Drospirenone (I) [step g)] can be performed, in a particular embodiment, with para-toluenesulfonic acid or potassium bisulfite in the presence of an organic solvent such as, for example, tetrahydrofuran, ethyl acetate, ethanol or dichloromethane. In a more particular embodiment, the reaction is carried out using para-toluenesulfonic acid in a medium comprising ethyl acetate.

In another preferred embodiment, the invention provides a process for obtaining Drospirenone (I) which comprises:

a) protecting a compound of formula (IVa)

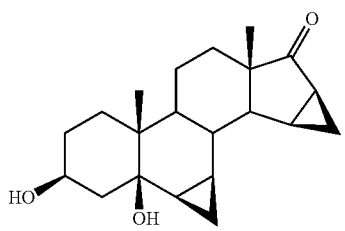

(IVa)

to render a compound of formula (IVb)

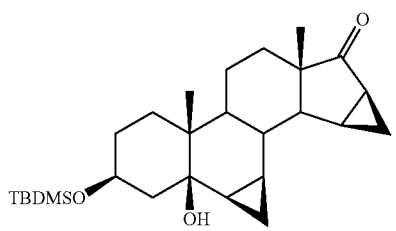

(IVb)

wherein TBDMS is tert-butyldimethylsilyl;

b) reacting a compound of formula (IVb) with a compound of formula (Va)

(Va)

to render a compound of formula (IIIb)

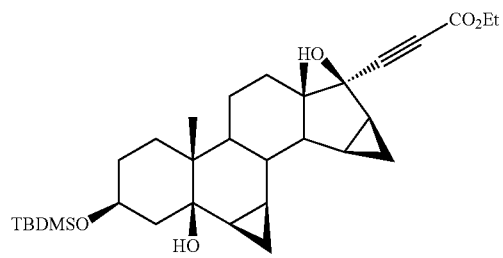

(IIIb)

wherein TBDMS is tert-butyldimethylsilyl;

c) deprotecting the protected hydroxyl group in position 3 of said compound of formula (IIIb) to render a compound of formula (IIIc)

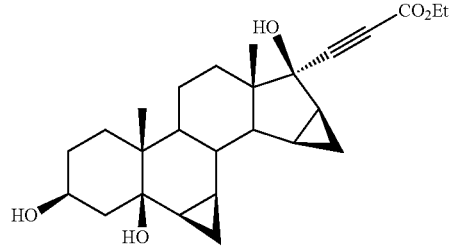

(IIIc)

d) oxidizing the hydroxyl group in position 3 of said compound of formula (IIIc) in the presence of an oxidizing species to yield a compound of formula (IIf):

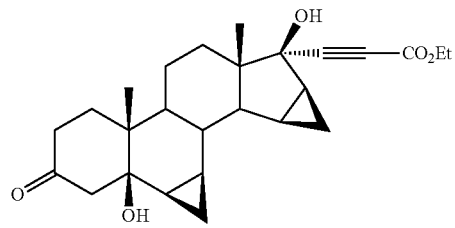

(IIf)

e) subjecting the compound of formula (IIf) to an elimination and saponification reaction to yield the intermediate of formula (IIi)

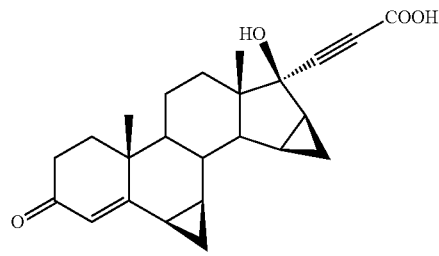

(IIi)

f) subjecting the compound of formula (IIi) to a hydrogenation reaction in the presence of a Pt or Pd catalyst to yield the intermediate of formula (IIj)

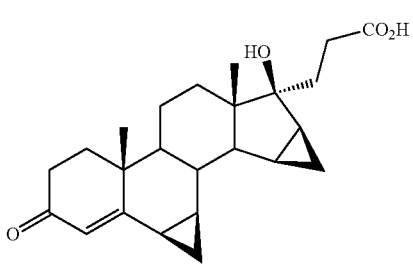

(IIj)

and g) subjecting the compound of formula (IIj) to treatment in the presence of an acid to render Drospirenone (I).

According to this preferred embodiment of the invention, the protection reaction of the compound of formula (IVa) to yield the compound of formula (IVb) [step a)], in a particular embodiment, is carried out using a TBDMS triflate or halide in the presence of a base and an organic solvent. In a preferred embodiment, the base is an organic base, preferably an amine, and the solvent is a suitable organic solvent such as an ether, a halogenated solvent or DMF. In a particular embodiment, the reaction takes place in the presence of TBDMS chloride using triethylamine as the base and DMF as the solvent.

In step b), the reaction conditions of the compound of formula (IVb) with the compound of formula (Va) to yield a compound of formula (IIIb) are the same as those mentioned above in relation to the process of the invention for obtaining the compounds of formula (III) [i.e., the process for obtaining a compound of formula (III) by reacting a compound of formula (IV) with a propargyl ester of formula (V)]. In a particular embodiment, the reaction is carried out in the presence of HMDSLi and an aromatic solvent, preferably toluene.

The deprotection of the hydroxyl in position 3 of a compound of formula (IIIb) to yield a compound of formula (IIIc) [step c)] can be carried out using fluoride salts such as pyridinium fluoride, potassium fluoride, ammonium fluoride or tetrabutylammonium fluoride. In a particular embodiment, the reaction is carried out using tetrabutylammonium fluoride in an ether solvent, preferably tetrahydrofuran.

The oxidation of the hydroxyl group in position 3 of the compound of formula (IIIc) to yield a compound of formula (IIf) [step d)] is preferably carried out in the presence of an oxidizing reagent such as, for example, TEMPO, calcium hypochlorite, trichloroisocyanuric acid or mixtures thereof. In a particular embodiment, the reaction is carried out using trichloroisocyanuric acid in the presence of TEMPO and a two phase system formed by a mixture of DCM/THF and water/sodium bicarbonate.

The dehydration step [step e)] of a compound of formula (IIf) to yield the intermediate of formula (III) takes place in a basic medium such as, for example, sodium carbonate, sodium hydroxide, lithium hydroxide (e.g., lithium hydroxide monohydrate), etc. in the presence of a solvent such as, for example, tetrahydrofuran, methyl-tetrahydrofuran, acetonitrile, methanol, isopropanol, toluene or water. In a particular embodiment, the reaction is carried out using lithium hydroxide monohydrate in a medium comprising water.

The hydrogenation reaction of the compound of formula (III) to render the intermediate of formula (IIj) [step f)], in a particular embodiment, is performed using a Pd/C or Pt/C, preferably Pt/C, as the catalyst in a hydrogen atmosphere, preferably at an overpressure, e.g., an overpressure of 0.1 bar ($10^4$ Pa), in the presence of ethyl acetate.

Finally, treatment of the compound of formula (IIj) to render Drospirenone (I) [step g)] can be performed, in a particular embodiment, with para-toluenesulfonic acid or potassium bisulfite in the presence of an organic solvent such as, for example, tetrahydrofuran, ethyl acetate, ethanol or dichloromethane. In a more particular embodiment, the reaction is carried out using para-toluenesulfonic acid in a medium comprising ethyl acetate.

In another aspect, the invention relates to a process for obtaining Drospirenone (I) which comprises providing a compound of formula (III) as defined above followed by d1) subjecting said compound of formula (III) to a hydrogenation reaction in the presence of a metal catalyst to yield the intermediate of formula (VI)

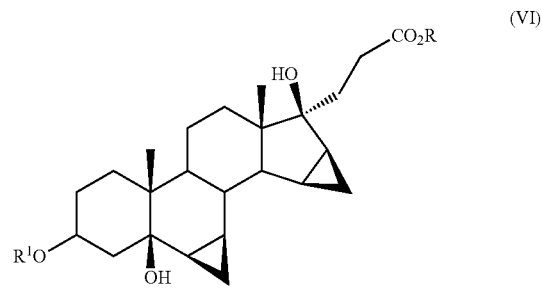

(VI)

wherein R is that previously defined, d2) deprotecting the hydroxyl group in position 3 of said compound of formula (VI) when $R^1$ is a protecting group, followed by a transesterification reaction to render the compound of formula (VII)

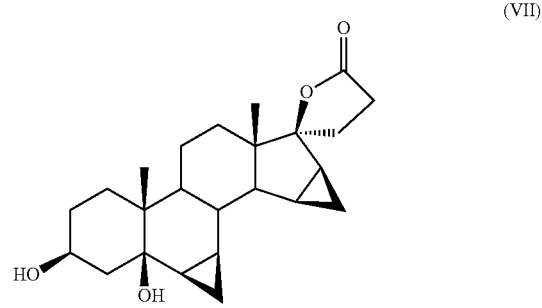 [SMILES: C[C@]12CCC3C(C1[C@@H]1C[C@@H]1[C@@]21CCC(=O)O1)[C@H]1C[C@H]1[C@]1(O)C[C@@H](O)CC[C@]31C]

(VII)

d3) oxidizing the compound of formula (VII) to render the compound of formula (IId)

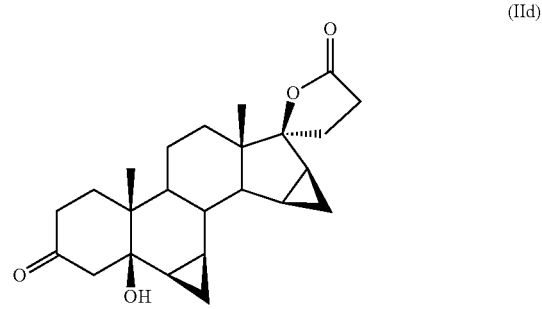 [SMILES: C[C@]12CCC3C(C1[C@@H]1C[C@@H]1[C@@]21CCC(=O)O1)[C@H]1C[C@H]1[C@]1(O)CC(=O)CC[C@]31C]

(IId)

and d4) subjecting the compound of formula (IId) to an elimination reaction to render Drospirenone (I).

In a particular embodiment, in the compound of formula (III), R is $C_1$-$C_6$ alkyl. In another particular embodiment, R is linear or branched $C_1$-$C_6$ alkyl, preferably $C_1$-$C_3$ alkyl, more preferably ethyl.

In another particular embodiment, in the compound of formula (III), $R^1$ is hydrogen. In another particular embodiment, in the compound of formula (III), $R^1$ represents a hydroxyl-protecting group such as, for example, a silyl group, particularly a tert-butyldimethylsilyl group or a trimethylsilyl group; an ether or an ester. In a particular embodiment, in the compound of formula (III), $R^1$ is selected from hydrogen and a silylated hydroxyl-protecting group, preferably hydrogen, trimethylsilyl or tert-butyldimethylsilyl.

In another particular embodiment, R is linear or branched $C_1$-$C_8$ alkyl and $R^1$ is selected from hydrogen and a silylated hydroxyl-protecting group. Preferably, R is $C_1$-$C_3$ alkyl and $R^1$ is selected from hydrogen, trimethylsilyl and tert-butyldimethylsilyl.

Particular embodiments of the invention include the use of compounds of formula (III) in which:
R is ethyl and $R^1$ is hydrogen; or
R is ethyl and $R^1$ is tert-butyldimethylsilyl; or
R is ethyl and $R^1$ is trimethylsilyl.

In a particular embodiment, the hydrogenation reaction d1) is carried out in the presence of a Pd or Pt catalyst, a Pd/C or Pt/C catalyst is preferably used.

In a preferred embodiment, the hydrogenation step d1) is performed using Pd/C as a catalyst at atmospheric pressure, using solvents such as ethanol or ethyl acetate, and preferably at room temperature.

The compounds of formula (VI) obtained can be used directly in the following step or alternatively they can be isolated or purified by feasible methods from the industrial point of view such as, for example, by means of crystallization or precipitation techniques, using solvents such as ethyl acetate, toluene or mixtures thereof with heptane. According to a particular embodiment, the intermediate of formula (VI) wherein R is an ethyl group and $R^1$ is a TBDMS group is purified by means of crystallization in ethyl acetate/heptane.

The compounds of formula (VI) wherein $R^1$ is hydrogen can be directly transformed into the compound of formula (VII) by treatment in acid medium, in which there is an intramolecular transesterification reaction to yield the corresponding lactone.

To establish the acid conditions, both organic and inorganic acids, such as for example para-toluenesulfonic acid or potassium bisulfate, in catalytic or equimolecular amounts, can be used, using solvents such as tetrahydrofuran, ethyl acetate, ethanol or dichloromethane, in which the reaction preferably takes place at room temperature.

The compound of formula (VII) obtained in d2) can be isolated or purified by means of crystallization or precipitation techniques, using for example a DMF/water mixture.

In the event that $R^1$ is a protecting group, such as a silyl-derivative, its prior elimination in step d2) by means of using acid media or by means of fluoride salts additionally causes the simultaneous formation of the lactone to give rise to compound of formula (VII).

In a particular embodiment, when $R^1$ is a silyl protecting group the deprotection step d2) is carried out using fluoride salts, inorganic acids such as hydrochloric acid in ethanol, organic acids such as formic acid in tetrahydrofuran or para-toluenesulfonic acid.

Particularly, when the protecting group $R^1$ is trimethylsilyl (TMS) or tert-butyldimethylsilyl (TBDMS), fluoride salts such as pyridinium fluoride, potassium fluoride, ammonium fluoride, etc., can be used for its elimination.

The oxidation reaction d3) providing the compound of formula (IId) can in turn be carried out by means of any oxidation reaction which allows transforming a hydroxyl group into a carbonyl group, following for example the processes described in U.S. Pat. No. 4,416,985, U.S. Pat. No. 6,121,465, EP 1571153 and EP 1828222, by means of using reagents such as TEMPO, calcium hypochlorite or trichloroisocyanuric acid.

In a particular embodiment, the transformation of the compound of formula (VII) into the corresponding ketone of formula (IId) is performed through the use of trichloro-isocyanuric acid in the presence of 2,2,6,6-tetramethyl-piperidine-1-oxide (TEMPO) in a two-phase system formed by a dichloromethane/tetrahydrofuran and water/sodium or potassium bicarbonate mixture at room temperature.

The compounds of formula (IId) obtained can be used directly or can be purified by means of conventional and industrially acceptable processes such as for example by means of a crystallization process. Illustrative non-limiting examples of suitable solvents for said crystallization include dichloromethane, heptane, toluene, methyl tert-butyl ether or mixtures thereof. In a preferred embodiment, said solvent is selected from dichloromethane, toluene and mixtures thereof with heptane. In a particular embodiment, the compound of formula (IId) can be crystallized in DCM or DCM/heptane.

Step d4) for transforming the compound of formula (IId) into Drospirenone can be performed by using the conditions described in U.S. Pat. No. 6,933,395 and EP 1746101.

Another aspect of the invention relates to the following intermediate compounds in the synthesis of Drospirenone (I):

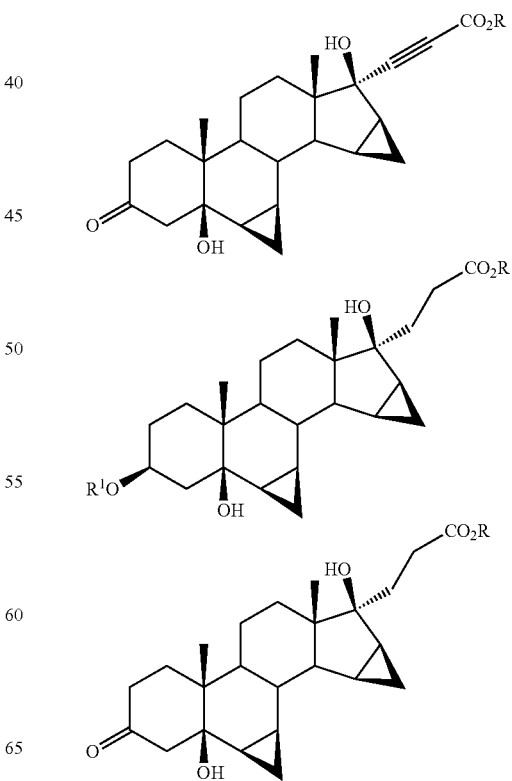

31

-continued

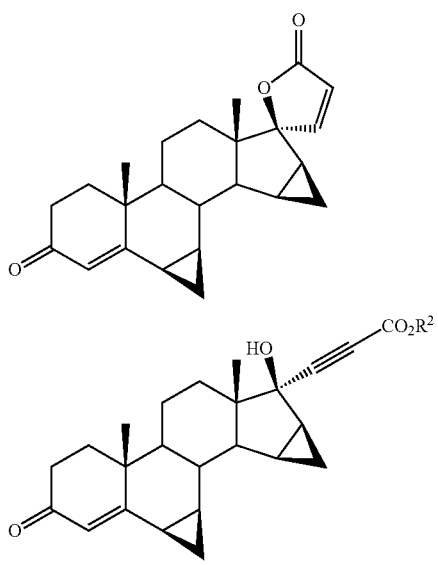

or a solvate thereof, wherein R, R$^1$ and R$^2$ are those previously defined.

In a particular embodiment, the intermediate compounds are selected from:

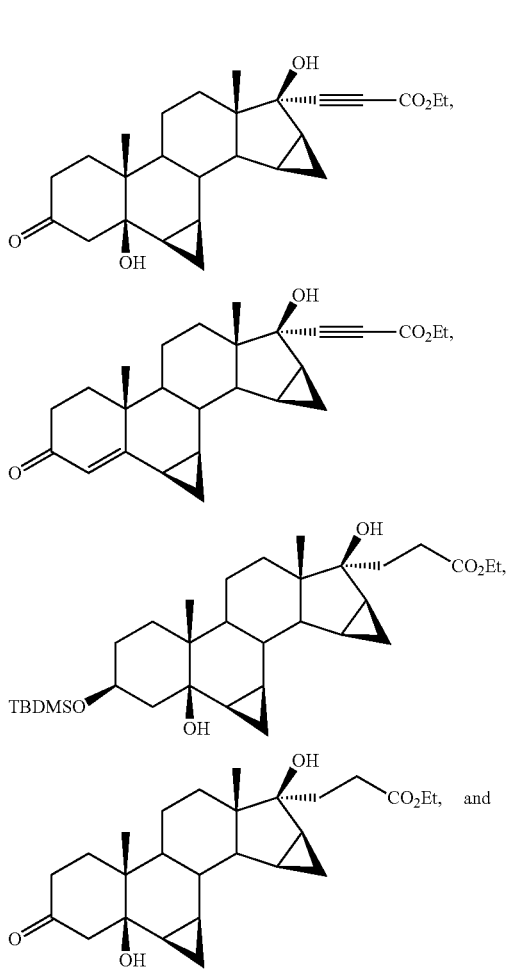

32

-continued

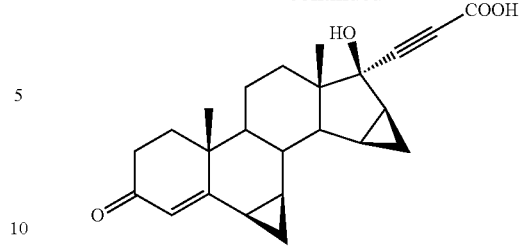

or a solvate thereof.

The following examples illustrate the invention and should not be considered as limitative of the invention.

EXAMPLES

Example 1

Synthesis of 6β,7β;15β,16β-dimethylene-3β-tert-butyldimethylsilyloxy-5β-hydroxy-androstan-17-one (IVb)

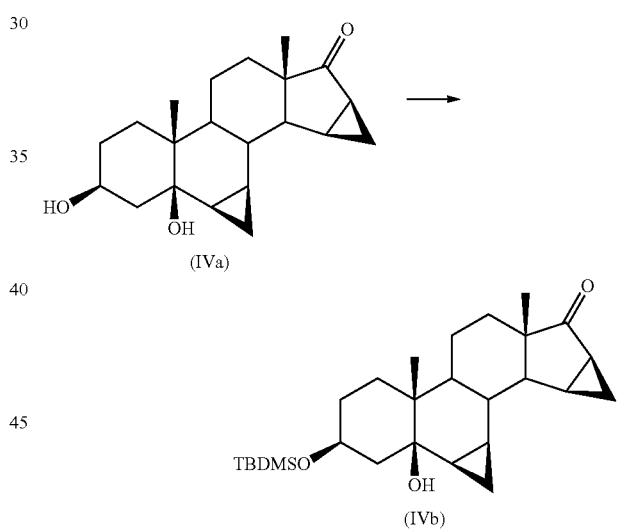

67.5 ml (0.48 moles) of triethylamine and 68.5 g (0.45 mol) of tert-butyldimethylsilyl chloride were added to a mixture under stirring, formed by 100 g (0.30 mol) of 6β,7β;15β,16β-dimethylene-3β,5β-dihydroxy-androstan-17-one (IVa) and 500 ml of dimethylformamide at room temperature, the resulting mixture was maintained under stirring for 45 minutes. Then, 2000 ml of water were added to the reaction mixture and maintained under stirring for half an hour, the obtained suspension was filtered and washed with another 1000 ml of water. The filtered solid was dried, obtaining 132.9 g of 6β,7β;15β,16β-dimethylene-3β-tert-butyldimethylsilyloxy-5β-hydroxy-androstan-17-one (IVb) (yield 98.8%). The product had the following spectroscopic characteristics:

¹H-NMR (400 MHz, 75° C., DMSO-d₆, δ): 0.05 (3H, s, CH₃—Si), 0.07 (3H, s, CH₃—Si), 0.40-1.70 (18H, m), 0.79 (3H, s), 0.84 (3H, s), 0.90 (9H, s, CH₃—C_Si), 2.00-2.20 (2H, m), 3.75 (1H, broad s), 4.05 (1H, broad s).

¹³C-NMR (100 MHz, 40° C., DMSO-d₆, δ): −5.2 (CH₃—Si), −5.0 (CH₃—Si), 10.2, 13.1, 17.1, 17.6, 18.6, 19.8, 21.3, 22.1, 25.3, 25.6 (3×CH₃—C—Si), 25.8, 28.1, 33.1, 34.9, 42.2, 44.1, 51.6, 68.5, 72.2, 214.0 (C=O).

Example 2

Synthesis of 6β,7β;15β,16β-dimethylene-3β-trimethylsilyloxy-5β-hydroxy-androstan-17-one (IVc)

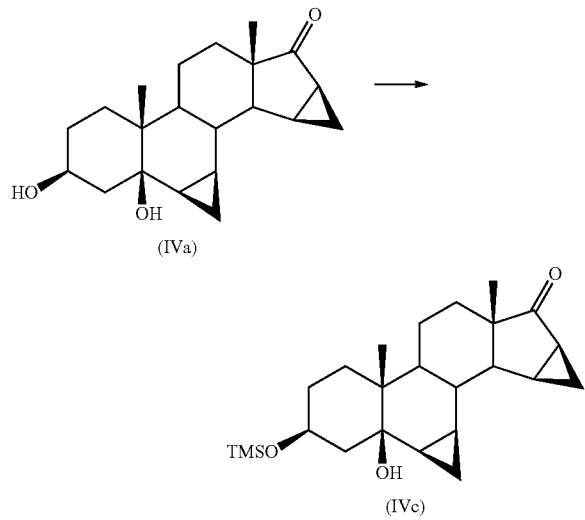

6.8 ml (0.048 mol) of triethylamine and 5.7 g (0.045 mol) of trimethylchlorosilane were added to a mixture under stirring formed by 10 g (0.03 mol) of 6β,7β;15β,16β-dimethylene-3β,5β-dihydroxy-androstan-17-one (IVa) and 50 ml of dimethylformamide at room temperature, the resulting mixture was maintained under stirring for 45 minutes. Then, 200 ml of water were added to the reaction mixture and maintained under stirring for half an hour, the obtained suspension was filtered and washed with another 100 ml of water. The filtered solid was dried, obtaining 12.0 g of 6β,7β;15β,16β-dimethylene-3β-trimethylsilyloxy-5β-hydroxy-androstan-17-one (IVc) (yield 98.5%). The product had the following spectroscopic characteristics:

¹H-NMR (400 MHz, DMSO-d₆, δ): 0.10 (9H, s, CH₃—Si), 0.40-1.00 (3H, m), 0.78 (3H, s (CH₃), 0.82 (3H, s (CH₃), 1.00-1.80 (15H, m), 1.90-2.20 (3H, m), 3.85 (1H, broad s), 3.97 (1H, broad s).

¹³C-NMR (100 MHz, DMSO-d₆, δ): 0.1 (3×CH₃—Si), 13.3, 17.1, 18.3, 19.7, 21.5, 22.2, 25.3, 33.2, 35.0, 42.1, 44.9, 51.8, 68.2, 71.9, 215.0 (C=O).

Example 3

Addition of ethyl propiolate. Synthesis of 6β,7β;15β,16β-dimethylene-3β-tert-butyldimethylsilyloxy-5β,17β-dihydroxy-17α-(2-ethoxycarbonyl)-ethynyl-androstane (IIIb)

a) By Direct Addition:

37.4 g (1.63 mol) of lithium amide were added to a stirred solution at room temperature and in an inert atmosphere, formed by 50 g (0.11 mol) of 6β,7β;15β,16β-dimethylene-3β-tert-butyldimethylsilyloxy-5β-hydroxy-androstan-17-one (IVb) and 1000 ml of toluene, and after another 15 minutes, 13.7 ml (0.13 mol) of ethyl propiolate were added, the reaction mixture was maintained under stirring for another 4 hours. Then, 30 ml of water were added and the solvent was distilled under reduced pressure until reaching a final volume of 250 mL. Then 750 ml of ethyl acetate and 1000 ml of water were added and the obtained mixture was maintained under stirring for half an hour. The two phases obtained were separated and the aqueous phase was extracted again with 250 ml of ethyl acetate. The organic phases obtained were pooled and washed successively with 1000 and 500 ml of water. Part of the solvent was removed under reduced pressure until reaching a final volume of 150 mL, 500 ml of heptane were added and part of the solvent was again removed under reduced pressure until a final volume of 150 ml. The obtained suspension was cooled at 5° C., filtered and washed with cold heptane. The obtained solid was dried and 51.7 g of 6β,7β;15β,16β-dimethylene-3β-tert-butyldimethylsilyloxy-5β,17β-dihydroxy-17β-(2-ethoxycarbonyl)-ethynyl-androstane (IIIb) were obtained in the form of toluene hemisolvate (yield 78.1%).

It was possible to obtain the desolvated product by dissolving the previously obtained hemisolvate in ethyl acetate and evaporating the solvent to dryness. The solid thus obtained was dried in an oven to provide the solvent-free form. The obtained product had the following spectroscopic properties:

Toluene hemisolvate: ¹H-NMR (400 MHz, 40° C., DMSO-d₆, δ): 0.02 (3H, s, CH₃—Si), 0.04 (3H, s, CH₃—Si), 0.20-0.30 (1H, m), 0.35-0.45 (1H, m), 0.50-0.80 (3H, m), 0.74 (6H, s, CH₃ 18+CH₃ 19), 0.84 (9H, s, 3×CH₃—C—Si), 0.95-1.15 (6H, m), 1.20 (3H, t, J=8.0 Hz, CH₃ Et), 1.25-1.70 (8H, m), 1.75-1.85 (1H, m), 2.00-2.10 (1H, m), 3.87 (1H, s, OH), 4.01 (1H, m, H3), 4.15 (2H, q, J=8.0 Hz, CH$_2$ Et), 5.95 (1H, s, OH).

Desolvated product: $^1$H-NMR (400 MHz, 40° C., DMSO-d$_6$, δ): 0.02 (3H, s, CH$_3$—Si), 0.04 (3H, s, CH$_3$—Si), 0.20-0.30 (1H, m), 0.35-0.45 (1H, m), 0.50-0.80 (3H, m), 0.74 (6H, s, CH3 18+CH3 19), 0.84 (9H, s, 3×CH3-C—Si), 0.95-1.15 (6H, m), 1.20 (3H, t, J=8.0 Hz, CH3 Et), 1.25-1.70 (8H, m), 1.75-1.85 (1H, m), 2.00-2.10 (1H, m), 3.87 (1H, s, OH), 4.01 (1H, m, H3), 4.15 (2H, q, J=8.0 Hz, CH2 Et), 5.95 (1H, s, OH).

$^{13}$C-NMR (100 MHz, 40° C., DMSO-d$_6$, δ): −5.2 (CH$_2$—Si), −4.9 (CH$_3$—Si), 8.8, 10.8, 11.2, 13.9, 14.2, 16.6, 17.6, 18.7, 19.7, 22.1, 22.6, 25.6 (3×CH$_3$—C—Si), 26.4, 28.2, 29.0, 33.6, 34.1, 38.5, 42.5, 44.3, 53.3, 61.8, 68.6, 72.1, 76.8, 78.3 (C≡), 91.4 (C≡), 153.1 (C=O).

b) By Reverse Addition:

0.5 g (0.001 mol) of 6β,7β;15β,16β-dimethylene-3β-tert-butyldimethylsilyloxy-5β-hydroxy-androstan-17-one (IVb) were added to a stirred solution at room temperature and in an inert atmosphere, formed by 0.37 g (0.016 mol) of lithium amide and 0.14 ml (0.0013 mol) of ethyl propiolate in 10 ml of toluene, and was maintained under stirring at the same temperature for 4 hours. The processing of the reaction was performed according to what is described in the previous example in which direct addition is used, to give rise to 0.5 g of 6β,7β;15β,16β-dimethylene-3β-tert-butyldimethylsilyloxy-5β,17β-dihydroxy-17β-(2-ethoxycarbonyl)-ethynyl-androstane (IIIb) in the form of toluene hemisolvate.

Example 3a

Synthesis of 6β,7β;15β,16β-dimethylene-3β-tert-butyldimethylsilyloxy-5β,17β-dihydroxy-17α-(2-ethoxycarbonyl)-ethynyl-androstane (IIIb)

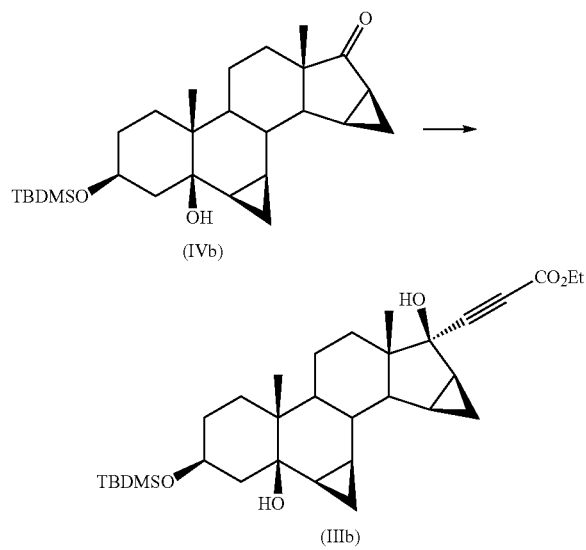

A solution was formed by 1.0 g (22 mmol) of 6β,7β;15β,16β-dimethylene-3β, tertbutyldimethylsilyloxy-5β-hydroxy-androstan-17-one (IVb) in 10 ml of toluene is cooled at a temperature between 0 and 5° C. and 0.46 ml of ethyl propiolate were added, the reaction mixture was maintained under stirring. Then, 4.5 ml (44 mmol) of HMDSLi 1M in THF were added to the stirred solution. Once the reaction had ended (approximately 30 minutes), 5 ml of water and 20 ml of ethyl acetate were added. The two phases obtained were separated. The solvent was removed under reduced pressure. The residue was purified by column chromatography to yield 0.77 g of 6β,7β;15β,16β-dimethylene-3β-tert-butyldimethylsilyloxy-5β,17β-dihydroxy-17β-(2-ethoxy-carbonyl)-ethynyl-androstane (IIIb) were obtained (yield 76.9%).

Example 4

Synthesis of 6β,7β;15β,16β-dimethylene-3β,5β 17β-trihydroxy-17α-(2-ethoxycarbonyl)-ethynyl-androstane (IIIc)

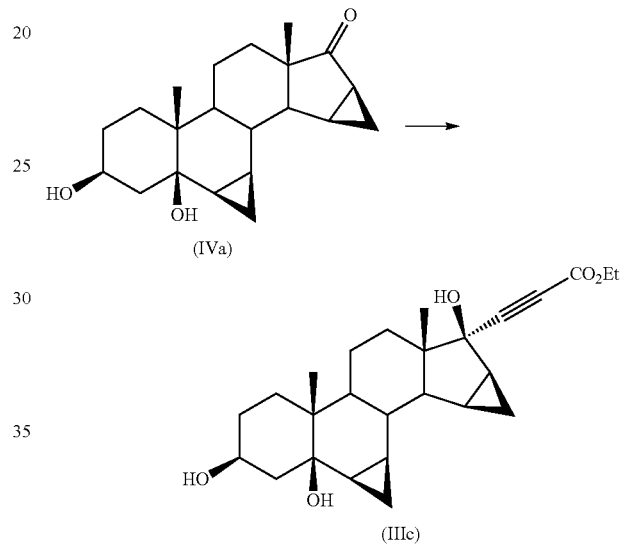

0.1 g (0.006 mol) of lithium amide were added to a stirred solution at room temperature and in an inert atmosphere, formed by 0.1 g (0.003 mol) of 6β,7β;15β,16β-dimethylene-3β,5β-dihydroxy-androstan-17-one (IVa) and 2 ml of toluene. After 15 minutes, 0.06 ml (0.0013 mol) of ethyl propiolate were added and the reaction mixture was maintained under stirring for 4 hours. Once the reaction had ended, 0.1 ml of water were added and the solvent was distilled under reduced pressure. The residue was purified by column chromatography to yield 0.05 g of 6β,7β;15β,16β-dimethylene-3β,5β,17β-trihydroxy-17α-(2-ethoxy-carbonyl)-ethynyl-androstane (IIIc) (45% molar yield). The product had the following spectroscopic properties:

$^1$H-NMR (400 MHz, DMSO-d$_6$, δ): 0.20-0.30 (1H, m), 0.35-0.45 (1H, m), 0.74 (6H, s, CH$_3$ 18+CH$_3$ 19), 1.21 (3H, t, J=8.0 Hz, CH3 Et), 0.55-1.75 (17H, m), 1.75-1.85 (1H, m), 2.00-2.10 (1H, m), 3.81 (1H, broad s, H3), 4.16 (2H, q, J=8.0 Hz, CH$_2$ Et), 4.30 (1H, broad s, OH), 4.78 (1H, broad s, OH), 5.93 (1H, broad s, OH).

$^{13}$C-NMR (100 MHz, DMSO-d$_6$, δ): 8.8, 10.9, 13.9, 14.3, 16.6, 18.1, 18.8, 22.0, 26.4, 28.0, 34.1, 38.5, 42.5, 43.8, 53.0, 61.9, 66.0, 72.5, 76.8, 78.3 (C≡), 91.4 (C≡), 153.1 (C=O).

Example 5

Synthesis of 6β,7β;15β,16β-dimethylene-3β,5β 17β-trihydroxy-17α-(2-ethoxycarbonyl)-ethynyl-androstane (IIIc)

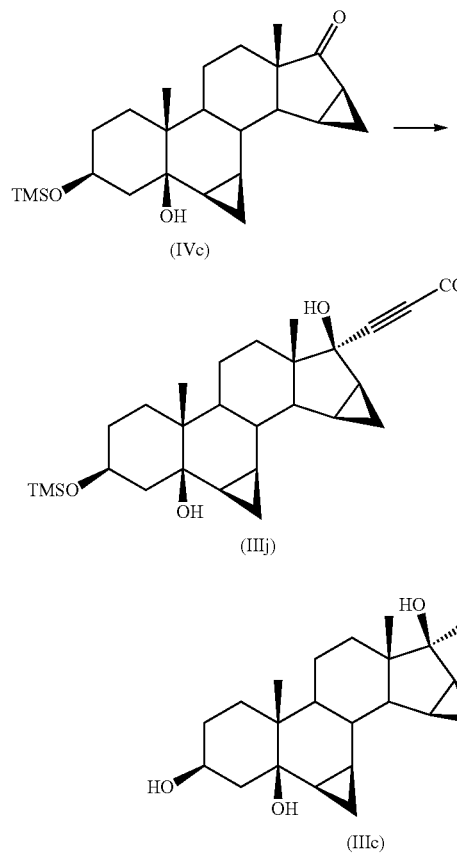

0.75 g (0.03 moles) of lithium amide were added to a stirred solution at room temperature and in an inert atmosphere, formed by 1 g (0.002 moles) of 6β,7β;15β,16β-dimethylene-3β-trimethylsilyloxy-5β-hydroxy-androstan-17-one (IVc) and 20 ml of toluene and after another 15 minutes, 0.27 ml (0.003 moles) of ethyl propiolate were added, the reaction mixture was maintained under stirring for another 4 hours. Once the reaction had ended, 0.1 ml of water were added and the solvent was distilled under reduced pressure. The residue was redissolved in tetrahydrofuran (10 ml) and 2 ml of a 1 M solution in THF (0.002 moles) of tetrabutylammonium fluoride were added. The reaction mixture was maintained under stirring at room temperature for one hour and 10 ml of water were subsequently added, the organic solvent was removed by distillation under reduced pressure and the resulting product was purified by silica gel column chromatography to provide 0.74 g of 6β,7β;15β,16β-dimethylene-3β,5β,17β-trihydroxy-17α-(2-ethoxycarbonyl)-ethynyl-androstane (IIIc) (70% molar yield).

Example 6

Synthesis of 6β,7β;15β,16β-dimethylene-3β,5β 17β-trihydroxy-17α-(2-ethoxycarbonyl)-ethynyl-androstane (IIIc) by the deprotection of (IIIb)

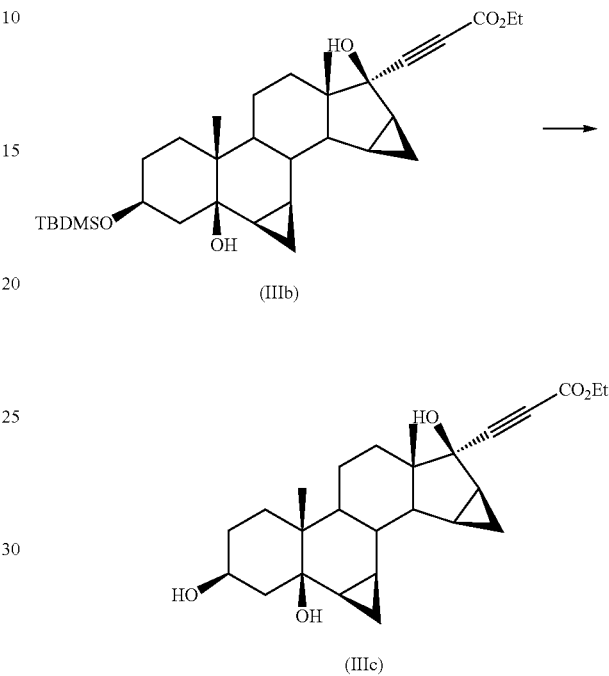

70 ml of a 1 M solution in THF (0.07 mol) of tetrabutylammonium fluoride were added to a solution formed by 37.5 g (0.064 mol) of 6β,7β;15β,16β-dimethylene-3β-tert-butyldimethylsilyloxy-5β,17β-dihydroxy-17α-(2-ethoxycarbonyl)-ethynyl-androstane (IIIb) in the form of toluene hemisolvate and 375 ml of THF. The reaction mixture was maintained under stirring at room temperature for one hour and 375 ml of water were subsequently added, the organic solvent was removed by distillation under reduced pressure, 375 ml of methylene chloride were added and the two phases obtained were separated. The organic phase was washed with 375 ml of water and distilled exchanging the solvent by addition of heptane. The obtained suspension was maintained under stirring at room temperature and the solid was finally isolated by filtration and washing with more heptane. The product was dried in an oven to obtain 27.14 g of 6β,7β;15β,16β-dimethylene-3β,5β,17β-trihydroxy-17α-(2-ethoxy-carbonyl)-ethynyl-androstane (IIIc) (yield 99.4%). The product had the following spectroscopic properties:

$^1$H-NMR (400 MHz, DMSO-$d_6$, δ): 0.20-0.30 (1H, m), 0.35-0.45 (1H, m), 0.74 (6H, s, CH$_3$ 18+CH$_3$ 19), 1.21 (3H, t, J=8.0 Hz, CH3 Et), 0.55-1.75 (17H, m), 1.75-1.85 (1H, m), 2.00-2.10 (1H, m), 3.81 (1H, broad s, H3), 4.16 (2H, q, J=8.0 Hz, CH2 Et), 4.30 (1H, broad s, OH), 4.78 (1H, broad s, OH), 5.93 (1H, broad s, OH).

Example 7

Synthesis of 6β,7β;15β,16β-dimethylene-5β 17β-dihydroxy-17α-(2-ethoxycarbonyl)-ethynyl-androstan-3-one (IIf)

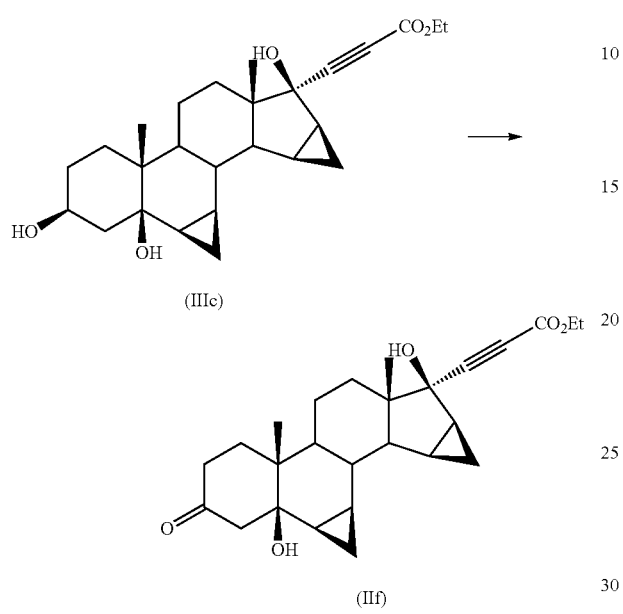

A solution formed by 37.5 g of sodium bicarbonate in 375 ml of water was added to a solution at room temperature and under stirring formed by 25 g (0.058 mol) of 6β,7β;15β,16β-dimethylene-3β,5β,17β-trihydroxy-17α-(2-ethoxycarbonyl)-ethynyl-androstane (IIIc), 425 ml of methylene chloride and 100 ml of THF. Then, 0.55 g (0.0035 mol) of 2,2,6,6-tetramethyl-piperidine-N-oxide (TEMPO) and 17.4 g (0.075 mol) of trichloroisocyanuric acid (TCCA) were added in portions to the two-phase mixture. The reaction mixture was maintained under stirring for 1 hour and the phases were separated, the aqueous phase was extracted once more with 50 ml of methylene chloride and the pooled organic phases were washed with an aqueous solution of 375 ml of sodium metabisulfite at 7% and with 375 ml of water. The solvent was removed by distillation under reduced pressure until reaching a final volume of 75 ml, 125 ml of heptane were added and the mixture of solvents was distilled again until a final volume of 75 ml. The obtained suspension was filtered and washed with heptane. 21.8 g of 6β,7β;15β,16β-dimethylene-5β,17β-dihydroxy-17α-(2-ethoxycarbonyl)-ethynyl-androstan-3-one (IIf) were obtained (yield 86.6%). The obtained product was also recrystallized using toluene. The product had the following spectroscopic properties:

$^1$H-NMR (400 MHz, DMSO-$d_6$, δ): 0.25-0.35 (1H, m), 0.40-0.55 (1H, m), 0.60-0.85 (3H, m), 0.77 (3H, s, $CH_3$), 0.78 (3H, s, $CH_3$), 0.95-1.20 (3H, m), 1.21 (3H, t, J=8.0 Hz, $CH_3$ Et), 1.30-1.70 (8H, m), 1.90-2.05 (2H, m), 2.10-2.25 (2H, m), 3.01 (1H, d, J=8.0 Hz, $H_{4a}$), 4.15 (2H, q, J=8.0 Hz, $CH_2$ Et), 4.52 (1H, broad s, OH), 5.96 (1H, broad s, OH).

$^{13}$C-NMR (100 MHz, DMSO-$d_6$, δ): 8.8 ($CH_2$), 12.0 ($CH_2$), 13.8 ($CH_3$), 15.6 (CH), 16.5 (CH), 17.5 ($CH_3$), 18.0 ($CH_3$), 21.6 ($CH_2$), 24.1 ($CH_2$), 26.4 ($CH_2$), 33.9 ($CH_2$), 34.0 ($CH_2$), 36.1 ($CH_2$), 38.2 ($CH_2$), 39.6 ($CH_2$), 42.6 (C), 45.4 (CH), 52.5 (C), 53.8 (CH), 61.8 ($CH_2$), 75.0 (C), 76.8 (C), 78.3 (≡C), 91.4 (≡C), 153.1 (COO), 210.2 (C=O, C3)

Example 8

Synthesis of 6β,7β;15β,16β-dimethylene-17β-dihydroxy-17α-(2-ethoxycarbonyl)-ethynyl-androst-4-en-3-one (IIg)

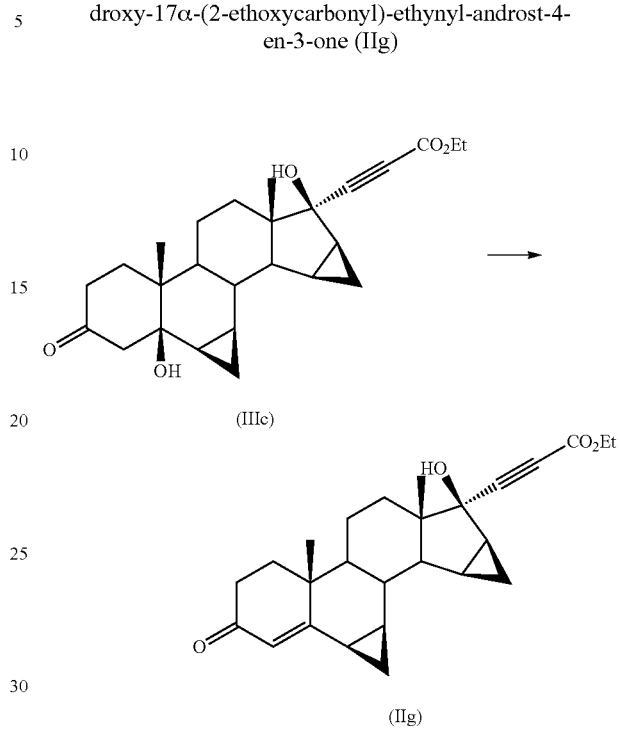

3.9 g (0.02 mol) of p-toluenesulfonic acid were added to a solution at room temperature formed by 17.5 g (0.041 mol) of 6β,7β;15β,16β-dimethylene-5β,17β-dihydroxy-17α-(2-ethoxy-carbonyl)-ethynyl-androstan-3-one (IIf) in 175 ml of tetrahydrofuran. The obtained mixture was maintained under stirring for 2 hours and was then neutralized with 2.8 ml (0.02 mol) of triethylamine. The solvent was removed by distillation under reduced pressure and 175 ml of toluene and 175 ml of water were added to the residue formed. The two phases obtained were separated and the organic phase was distilled until reaching a final volume of 105 ml, 175 ml of heptane were then added. The solvent was distilled until a final volume of 105 ml and the product was precipitated by adding heptane. It was maintained under stirring at room temperature for one hour, filtered and washed with heptane. The product was dried in an oven and 18.2 g of 6β,7β;15β,16β-dimethylene-17β-dihydroxy-17α-(2-ethoxy-carbonyl)-ethynyl-androst-4-en-3-one (IIg) were obtained in the form of toluene solvate (yield 75.4%). The isolated product has the following spectroscopic properties:

Toluene solvate: $^1$H-NMR (400 MHz, DMSO-$d_6$, δ): 0.30-0.40 (1H, m), 0.81 (3H, s, $CH_3$ 18), 0.75-0.85 (2H, m), 0.90-1.05 (2H, m), 1.00 (3H, s, $CH_3$ 19), 1.05-1.15 (3H, m), 1.20 (3H, t, J=8.0 Hz, $CH_3$ Et), 1.40-1.70 (7H, m), 1.70-1.80 (1H, m), 1.90-1.95 (1H, m), 2.10-2.25 (1H, m), 2.27 (3H, s, $CH_3$ Tol), 2.40-2.55 (1H, m), 4.15 (2H, q, J=8.0 Hz, $CH_2$ Et), 5.87 (1H, s, H4), 6.00 (1H, broad s, OH), 7.10-7.25 (5H, H Ar, Tol).

$^{13}$C-NMR (75 MHz, DMSO-$d_6$, δ): 9.5 ($CH_2$), 14.5 ($CH_3$), 16.2 (CH), 16.9 ($CH_3$), 17.8 ($CH_3$), 18.6 ($CH_2$), 19.1 (CH), 20.1 (CH), 21.4 ($CH_2$), 21.7 ($CH_3$), 27.0 (CH), 34.3 ($CH_2$), 34.7 (CH), 37.1 ($CH_2$), 37.6 ($CH_2$), 38.7 (C), 43.0 (C), 52.0 (CH), 53.0 (CH), 62.5 ($CH_2$), 77.5 (≡C), 78.9 (≡C), 91.7 (C

17), 125.6 (C4), 125.9 (CH Ar, Tol), 128.8 (2×CH Ar, Tol), 128.5 (2×CH Ar, Tol), 138.0 (C Ar, Tol), 153.7 (C5), 171.9 (COO), 197.0 (C3).

The product can be obtained in desolvated form. To that end, the solvate was stirred in ethyl acetate for 1 hour, filtered and washed with ethyl acetate.

Example 8a

Synthesis of 6β,7β;15β,16β-dimethylene-17β-dihydroxy-17α-(2-ethoxycarbonyl)-ethynyl-androst-4-en-3-one (IIg)

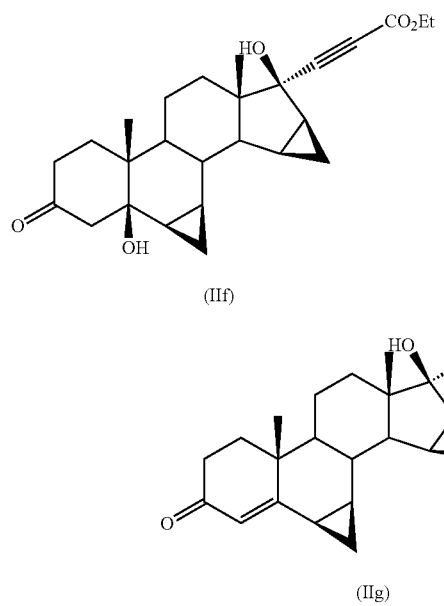

(IIf)

(IIg)

A solution was formed by 10.0 g (0.024 mol) of 6β,7β;15β, 16β-dimethylene-5β,17β-dihydroxy-17α-(2-ethoxy-carbonyl)-ethynyl-androstan-3-one (IIf) in 60 ml of methanol at room temperature. The solution was cooled to 0/5° C. and 4.5 g (0.043 mol) of sodium carbonate was added to the solution under stirring.

The obtained mixture was maintained under stirring for 2 hours and was then adjusted to pH 7 with a solution of hydrochloric acid 1M. The solvent was removed by distillation under reduced pressure and 50 ml of dichloromethane was added.

The two phases obtained were separated and the aqueous phase was then adjusted to pH 3 with a solution of hydrochloric acid 1M and was extracted twice with dichloromethane.

The organic phases were distilled and 50 ml of toluene were added. The suspension was cooled to 0° C., maintained under stirring, filtered and washed with toluene.

The product (IIg) was obtained in the form of toluene solvate (yield 54%).

Example 8b

Synthesis of 6β,7β;15β,16β-dimethylene-17β-dihydroxy-17α-(2-carbonyl)-ethynyl-androst-4-en-3-one (IIi)

(IIf)

(IIi)

A suspension was formed by 10.0 g (0.024 mol) of 6β,7β; 15β,16β-dimethylene-5β,17β-dihydroxy-17α-(2-ethoxycarbonyl)-ethynyl-androstan-3-one (IIf) in 60 ml of water at room temperature. 2.0 g (0.048 mol) of lithium hydroxide monohydrate was added to the suspension under stirring.

The obtained mixture was maintained under stirring for 15 hours and was then adjusted to pH 1 with a solution of hydrochloric acid 1M, 60 ml of ethyl acetate was added. The two phases obtained were separated. The organic phases were distilled and 60 ml of toluene were added. The toluene phase was distilled up to 30 ml. The suspension was cooled to 0° C., maintained under stirring, filtered and washed with toluene.

The product (III) was obtained in the form of toluene solvate (yield 96%).

$^1$H-NMR (400 MHz), δ: 0.32 (1H, q, J=8.0 Hz), 0.80 (3H, s, H18), 0.75-0.85 (2H, m), 1.00 (3H, s, H19). 0.90-1.05 (2H, m), 1.05-1.25 (2H, m), 1.40-1.70 (1H, m), 1.70-1.80 (1H, m), 1.94 (1H, dd, J=2.0, 8.0 Hz), 2.15 (1H, d, J=16.0 Hz, H2), 2.40-2.60 (1H, m, H2), 5.87 (1H, s, H4), 5.92 (1H, broad s, OH), 13.5 (1H, broad s, COOH). Toluene peaks: 2.26 (3H, m, 3H), 7.05-7.25 (5H, m, H—Ar).

$^{13}$C-NMR (100 MHz), δ: 8.9 (CH$_2$), 16.2 (CH), 17.1 (CH3 C18), 18.0 (CH3 C19), 18.5 (CH2), 18.6 (CH), 19.6 (CH2), 20.7 (CH), 26.4 (CH), 33.7 (CH2), 34.1 (CH), 36.5 (C, C18), 37.0 (CH2), 38.0 (CH2, C2), 42.3 (C, C19), 51.3 (CH), 52.2 (CH), 78.0 (≡C), 78.1 (≡C), 89.8 (C, C17), 124.9 (CH, C4), 154.4 (C, C5), 171.3 (C, COOH), 196.4 (C, C3).

MS (m/z): 381 (M+1, 100%).

Example 9

Synthesis of 6β,7β;15β,16β-dimethylene-3-oxo-17α-pregn-4-ene-21,17-carbolactone (Drospirenone (I))

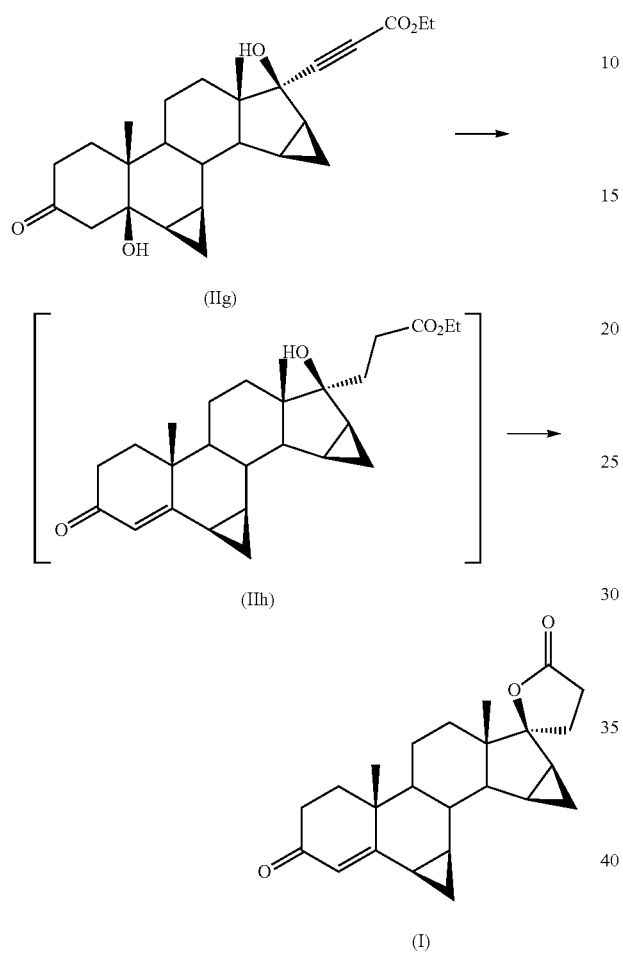

Example 9a

Synthesis of 6β,7β;15β,16β-dimethylene-3-oxo-17α-pregn-4-ene-21,17-carbolactone (Drospirenone (I))

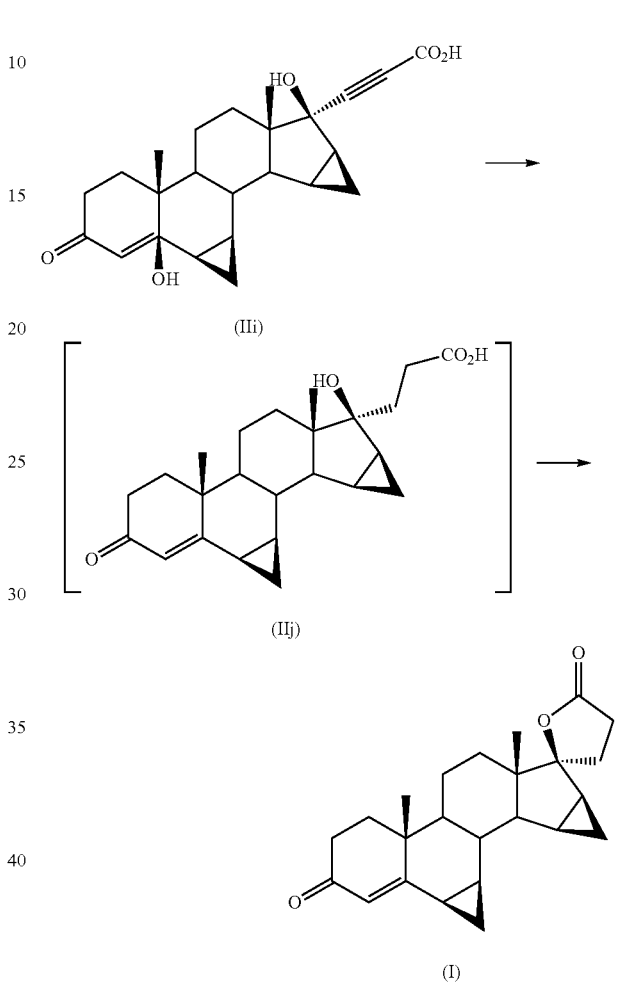

0.45 g of 5% Pt/C (50% moisture) were added to a solution formed by 9 g (0.018 mol) of 6β,7β;15β,16β-dimethylene-17β-dihydroxy-17α-(2-ethoxycarbonyl)-ethynyl-androst-4-en-3-one (IIg) and 180 ml of ethyl acetate. The system was first purged with nitrogen and then with hydrogen and stirred under a hydrogen atmosphere at an overpressure of 0.1 bar for 75 minutes. The catalyst was eliminated by filtration and washed with 180 ml of ethyl acetate. 0.9 g (0.0036 mol) of p-toluenesulfonic acid were added to the filtered solution of 6β,7β;15β,16β-dimethylene-17β-dihydroxy-17α-(2-ethoxycarbonyl)-ethyl-androst-4-en-3-one (IIh) and maintained under stirring at room temperature for 1 hour. It was neutralized by adding 0.63 ml (0.0036 mol) of triethylamine and 30 ml of water were then added, two phases were obtained which were then decanted. The solvent was eliminated under reduced pressure and was changed for isopropyl acetate until a final volume of 45 ml. It was cooled to 0/5° C., filtered and washed with isopropyl acetate. 4.5 g of 6β,7β;15β,16β-dimethylene-3-oxo-17β-pregn-4-ene-21,17-carbolactone (drospirenone) (I) were obtained. The product thus obtained had a purity greater than 99%. It was possible to increase the purity of the obtained product by recrystallizations in isopropyl acetate.

0.5 g of 5% Pt/C (50% moisture) were added to a solution formed by 5 g (0.01 mol) of 6β,7β;15β,16β-dimethylene-17β-dihydroxy-17α-(2-carbonyl)-ethynyl-androst-4-en-3-one (III) and 100 ml of ethyl acetate. The system was first purged 10 minutes with nitrogen and then with hydrogen and stirred under a hydrogen atmosphere at an overpressure of 0.15 bar for 4 hours. The catalyst was eliminated by filtration and washed with 100 ml of ethyl acetate. 0.05 g (0.0002 mol) of p-toluenesulfonic acid were added to the filtered solution of 6β,7β;15β,16β-dimethylene-17β-dihydroxy-17α-(2-carbonyl)-ethyl-androst-4-en-3-one (IIj) and maintained under stirring at room temperature for 1 hour. It was neutralized by adding 0.05 ml (0.0003 mol) of triethylamine and 15 ml of water were then added; two phases were obtained which were then decanted. The solvent was eliminated under reduced pressure and was changed for isopropyl alcohol. It was cooled to a temperature between 0° C. and 5° C., filtered and washed with isopropyl alcohol. 3.0 g of 6β,7β;15β,16β-dimethylene-3-oxo-17α-pregn-4-ene-21,17-carbo-lactone (Drospirenone (I)) were obtained.

Example 10

Synthesis of 6β,7β;15β,16β-dimethylene-3-oxo-17α-pregn-4,20-diene-21,17-carbolactone (20Δ-drospirenone (IIb))

a) Starting from 6β,7β;15β,16β-dimethylene-5β,17β-dihydroxy-17α-(2-ethoxycarbonyl)-ethynyl-androstan-3-one (IIf).

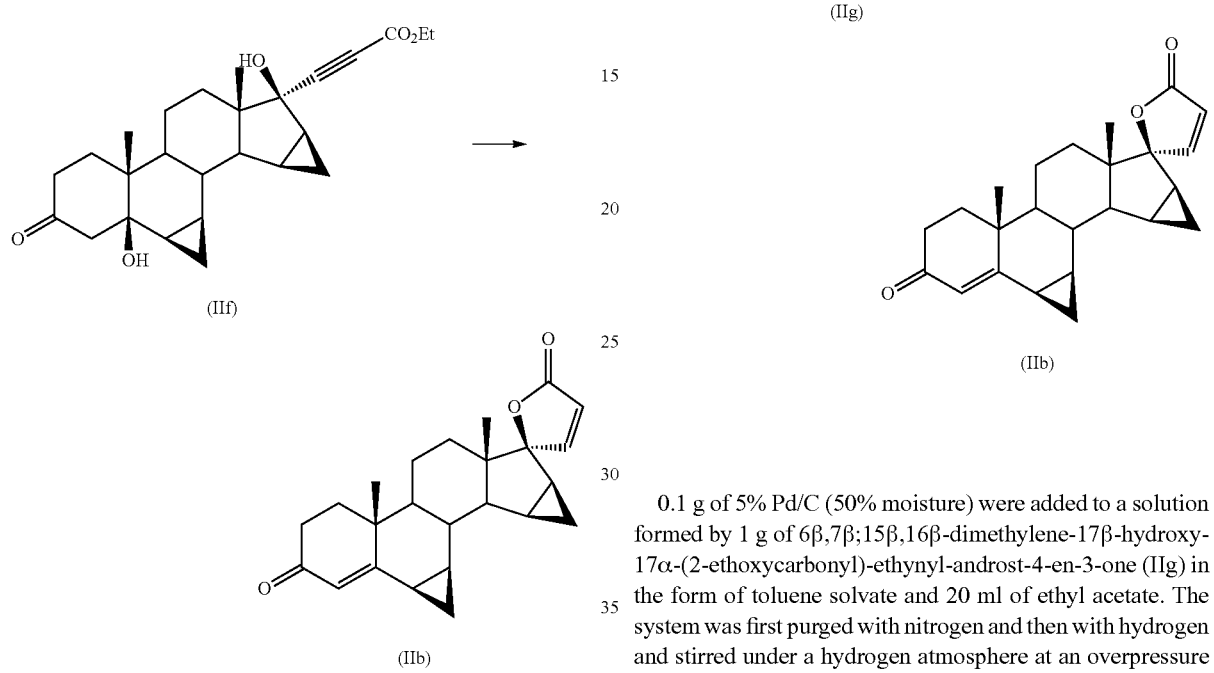

0.1 g of 5% Pd/C (50% moisture) were added to a solution formed by 1 g of 6β,7β;15β,16β-dimethylene-5β,17β-dihydroxy-17α-(2-ethoxycarbonyl)-ethynyl-androstan-3-one (IIf) and 20 ml of ethyl acetate. The system was first purged with nitrogen and then with hydrogen and was maintained under stirring under a hydrogen atmosphere at an overpressure of 0.1 bar for 1 hour. The catalyst was filtered and washed with ethyl acetate. The solvent was evaporated to dryness and the resulting residue was redissolved in 3 ml of dimethylformamide, the product was then precipitated by adding 10 ml of water. The obtained suspension was filtered and washed with water to obtain 0.6 g of 6β,7β;15β,16β-dimethylene-3-oxo-17α-pregn-4,20-diene-21,17-carbolactone (20β-drospirenone) (IIb) (yield: 70%). The isolated product had the following spectroscopic properties:

$^1$H-NMR (400 MHz, DMSO-$d_6$, δ): 0.45-0.60 (1H, m), 0.70-1.00 (3H, m), 0.91 (3H, s, $CH_3$), 1.01 (3H, s, $CH_3$), 1.00-1.30 (6H, m), 1.30-1.80 (5H, m), 2.10-2.20 (1H, m), 2.30-2.35 (1H, m), 5.90 (1H, s, H4), 6.12 (1H, d, J=8.0 Hz), 7.93 (1H, d, J=8.0 Hz).

$^{13}$C-NMR (100 MHz, DMSO-$d_6$, δ): 9.0, 16.4, 17.0, 18.4, 18.5, 19.3, 20.1, 20.6, 20.8, 33.6, 36.6, 36.9, 41.1, 51.2, 98.1, 118.2, 125.0, 159.8, 171.1, 172.2, 196.4.

b) Starting from 6β,7β;15β,16β-dimethylene-17β-hydroxy-17α-(2-ethoxycarbonyl)-ethynyl-androst-4-en-3-one (IIg).

0.1 g of 5% Pd/C (50% moisture) were added to a solution formed by 1 g of 6β,7β;15β,16β-dimethylene-17β-hydroxy-17α-(2-ethoxycarbonyl)-ethynyl-androst-4-en-3-one (IIg) in the form of toluene solvate and 20 ml of ethyl acetate. The system was first purged with nitrogen and then with hydrogen and stirred under a hydrogen atmosphere at an overpressure of 0.1 bar for 1 hour. The catalyst was filtered and washed with ethyl acetate. The solvent was evaporated to dryness to provide 0.65 g of 6β,7β;15β,16β-dimethylene-3-oxo-17α-pregn-4,20-diene-21,17-carbolactone (20Δ-drospirenone (IIb)) (Yield: 89%).

Example 11

Synthesis of drospirenone (I) from 20Δ-drospirenone (IIb)

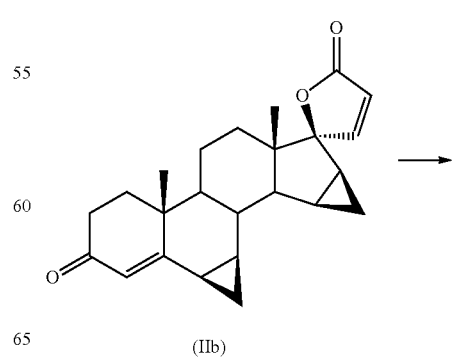

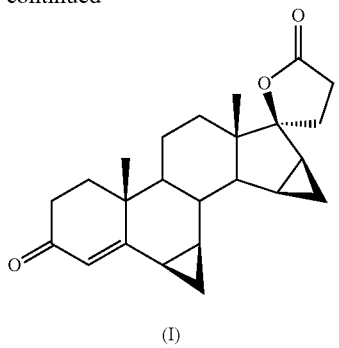

(I)

0.1 g of 5% Pt/C (50% moisture) were added to a solution formed by 1 g (0.003 mol) of 20Δ-drospirenone (IIb) in 20 ml of ethyl acetate. The system was first purged with nitrogen and then with hydrogen and stirred under a hydrogen atmosphere at an overpressure of 0.1 bar for 1 hour. The catalyst was filtered and washed with ethyl acetate. The solvent was evaporated to dryness to provide 0.9 g of Drospirenone (I) (yield 90%).

Example 12

Synthesis of 6β,7β;15β,16β-dimethylene-3β-tert-butyldimethylsilyloxy-5β,17β-dihydroxy-17α-(2-ethoxycarbonyl)-ethyl-androstane (VIb)

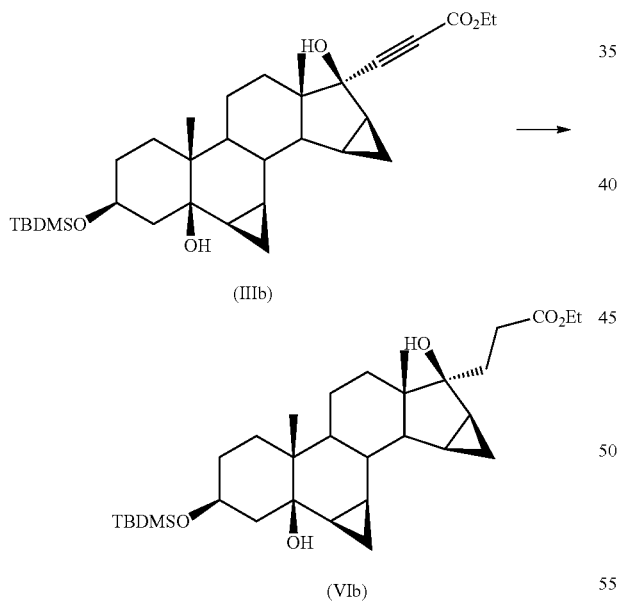

1.5 g of 5% Pd/C (50% moisture) were added to a solution formed by 15 g (0.026 mol) of 6β,7β;15β,16β-dimethylene-3β-tert-butyldimethylsilyloxy-5β,17β-dihydroxy-17β-(2-ethoxycarbonyl)-ethynyl-androstane (IIIb) in the form of toluene hemisolvate and 150 ml of ethyl acetate. The system was first purged with nitrogen and then with hydrogen and stirred under a hydrogen atmosphere at an overpressure of 0.1 bar for 1 hour. The catalyst was filtered, the solid was washed with ethyl acetate and the solvent was evaporated until reaching a residue. 12.4 g of 6β,7β;15β,16β-dimethylene-3β-tert-butyldimethylsilyloxy-5β,17β-dihydroxy-17α-(2-ethoxycarbonyl)-ethyl-androstane (VIb) were thus obtained (yield 90%). The isolated product had the following spectroscopic properties:

$^1$H-NMR (400 MHz, DMSO-d$_6$, δ): 0.02 (3H, s, CH$_3$—Si), 0.04 (3H, s, CH$_3$—Si), 0.35-0.45 (1H, m), 0.55-0.65 (1H, m), 0.74 (6H, s, 2×CH$_3$), 0.87 (9H, s, CH$_3$—C—Si), 0.70-0.90 (4H, m), 1.16 (3H, t, J=8.0 Hz, CH$_3$ Et), 1.00-1.80 (18H, m), 2.05-2.15 (1H, m), 3.84 (1H, broad s, OH), 4.02 (2H, q, J=8.0 Hz, CH$_2$ Et), 4.28 (1H, broad s, OH).

$^{13}$C-NMR (100 MHz, DMSO-d$_6$, δ): −5.3 (CH$_3$—Si), −5.0 (CH$_3$—Si), 7.9, 14.1, 14.3, 15.8, 17.6, 18.7, 19.3, 22.0, 25.6, 27.9, 29.1, 32.2, 34.1, 36.4, 42.2, 44.0, 52.6, 59.6, 68.6, 72.3, 80.2, 173.8.

Example 13

Synthesis of 6β,7β;15β,16β-dimethylene-3β,5β-dihydroxy-17α-pregnano-21,17-carbolactone (VII)

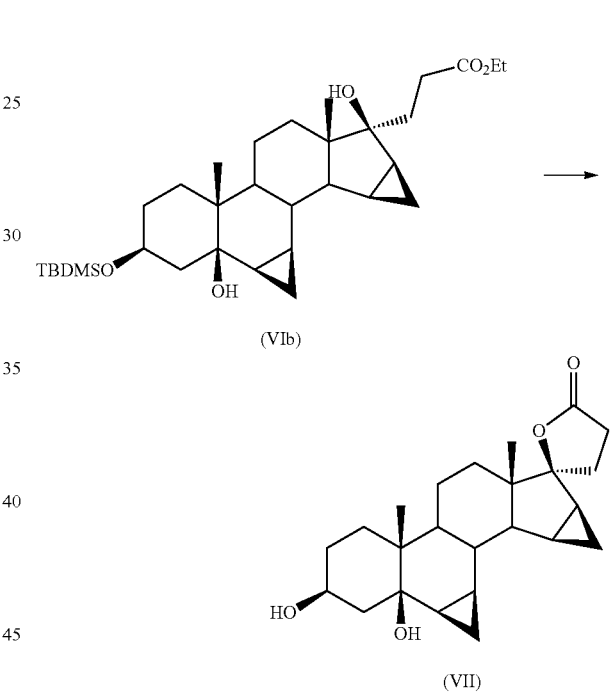

22 ml (0.022 mol) of a 1 M solution of tetrabutylammonium fluoride in THF were added to a solution at room temperature formed by 11 g (0.02 mol) of 6β,7β;15β,16β-dimethylene-3β-tert-butyldimethylsilyloxy-5β,17β-dihydroxy-17α-(2-ethoxycarbonyl)-ethyl-androstane (VIb) and 220 ml of THF, the reaction mixture was maintained under stirring for at least 1 hour. Once the reaction had ended, 220 ml of water were added and the organic solvent was removed by distillation under reduced pressure, 220 ml of methylene chloride were then added and the two phases formed were separated by decantation. The organic phase was distilled to a residue giving rise to 7.6 g of 6β,7β;15β,16β-dimethylene-3β,5β-dihydroxy-17α-pregnano-21,17-carbolactone (VII) (yield 87.5%). The isolated product had the following spectroscopic properties:

$^1$H-NMR (400 MHz, DMSO-d$_6$, δ): 0.25-0.50 (2H, m), 0.55-0.70 (2H, m), 0.75 (3H, s, CH$_3$), 0.77 (3H, s, CH$_3$), 0.80-1.50 (10H, m), 1.50-1.75 (4H, m), 1.75-1.80 (1H, m), 1.95-2.05 (2H, m), 2.25-2.60 (4H, m), 3.81 (1H, broad s), 4.33 (1H, broad s), 4.80 (1H, broad s).

$^{13}$C-NMR (100 MHz, DMSO-d$_6$, δ): 9.9, 10.9, 14.1, 16.5, 18.7, 19.6, 21.7, 23.7, 27.8, 28.9, 30.0, 33.6, 36.6, 39.8, 41.2, 44.0, 45.1, 51.4, 65.9, 72.6, 95.8, 176.4.

Example 14

Synthesis of 6β,7β;15β,16β-dimethylene-3-oxo-5β-hydroxy-17α-pregnano-21,17-carbolactone (IId)

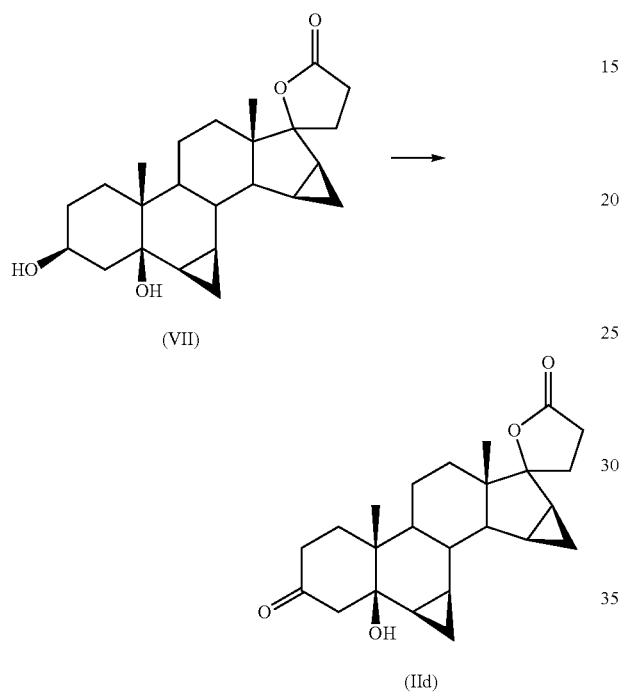

A solution of 10 g of sodium bicarbonate in 100 ml of water was added to a solution formed by 7 g (0.016 mol) of 6β,7β;15β,16β-dimethylene-3β,5β-dihydroxy-17α-pregnano-21,17-carbolactone (VII), 120 ml of methylene chloride and 28 ml of tetrahydrofuran, and was maintained under stirring enough so that the two phases were mixed at room temperature while 0.15 g (0.00096 mol) of 2,2,6,6-tetramethyl-piperidine-N-oxide (TEMPO) and 4.84 g (0.021 mol) of trichloroisocyanuric acid (TCCA) were added in portions. The reaction mixture was maintained under stirring for at least another hour, the phases were decanted and the organic phase was washed successively with a 7% aqueous solution of 100 ml of sodium metabisulfite and 100 ml of water. The obtained organic phase was distilled under reduced pressure until a final volume of 20 ml, 70 ml of heptane were then added, where a suspension was formed which was filtered, the obtained solid was washed with heptane and dried to obtain 5.6 g of 6β,7β;15β,16β-dimethylene-3-oxo-5β-hydroxy-17α-pregnano-21,17-carbolactone (IId) (yield, 80%). The isolated product had the following spectroscopic properties:

$^1$H-NMR (400 MHz, DMSO-d$_6$, δ): 0.35-0.45 (1H, m), 0.45-0.60 (1H, m), 0.60-0.75 (2H, m), 0.78 (3H, s, CH$_3$), 0.81 (3H, s, CH$_3$), 1.00-1.20 (3H, m), 1.25-1.75 (8H, m), 1.90-2.10 (3H, m), 2.10-2.20 (2H, m), 2.30-2.50 (3H, m), 2.50-2.60 (1H, m), 2.97 (1H, d, J=8.0 Hz H$_4$), 4.50 (1H, broad s, OH).

$^{13}$C-NMR (100 MHz, DMSO-d$_6$, δ): 10.2, 12.7, 15.8, 17.0, 18.1, 20.3, 22.0, 24.4, 24.9, 29.5, 30.7, 34.2, 34.4, 36.8, 37.1, 41.9, 45.8, 51.6, 54.4, 75.8, 96.4, 177.0, 210.7.

Example 15

Synthesis of drospirenone (I) from 6β,7β;15β,16β-dimethylene-3-oxo-5β-hydroxy-17α-pregnano-21,17-carbolactone (IId)

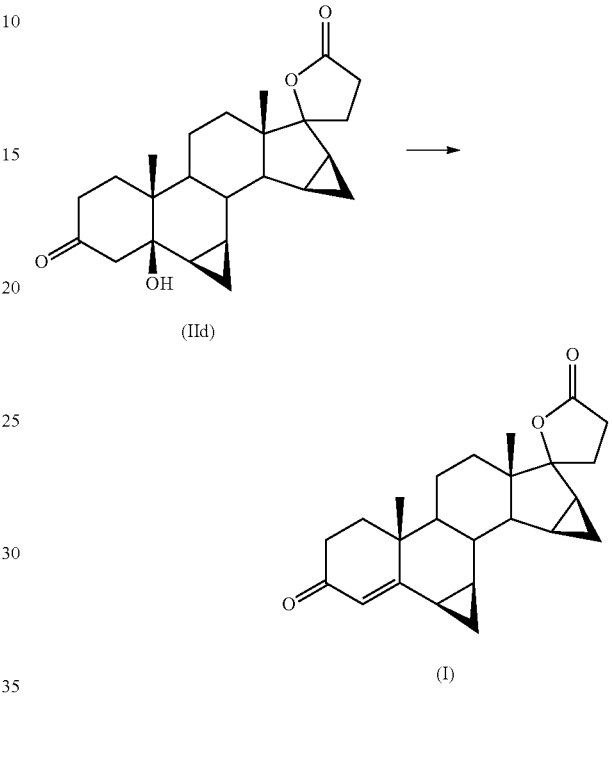

Drospirenone (I) was obtained by eliminating the hydroxyl group in position 5 using the conditions already described for example in U.S. Pat. No. 6,933,395 column 6.

Example 16

Synthesis of drospirenone (I) from 6β,7β;15β,16β-dimethylene-5β,17β-dihydroxy-17α-(2-ethoxycarbonyl)-ethynyl-androstan-3-one (IIf)

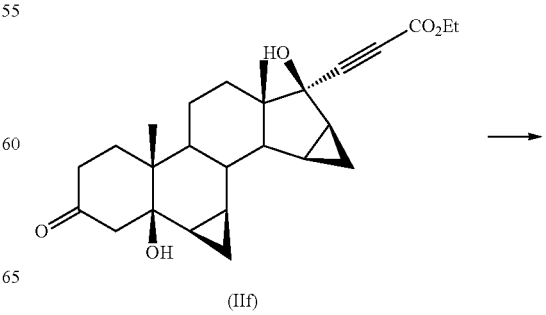

-continued

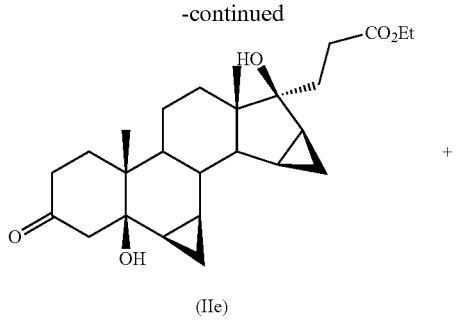

(IIe)

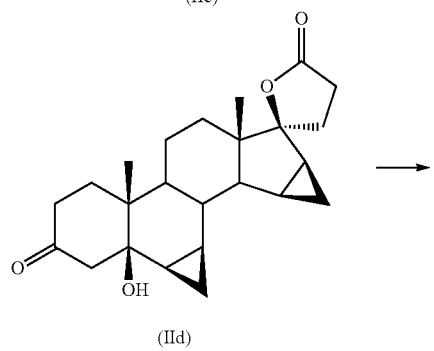

(IId)

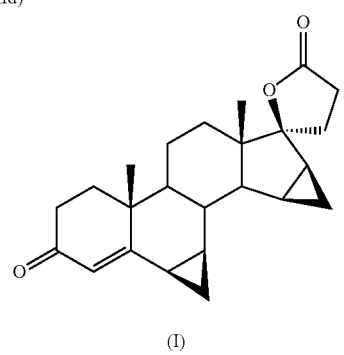

(I)

0.2 g of 5% Pt/C (50% moisture) were added to a solution formed by 1 g of 6β,7β;15β,16β-dimethylene-5β,17β-dihydroxy-17α-(2-ethoxycarbonyl)-ethynyl-androstan-3-one (IIf) and 20 ml of ethyl acetate. The system was first purged with nitrogen and then with hydrogen and was maintained under stirring under a hydrogen atmosphere at an overpressure of 0.1 bar for 1 hour. The catalyst was filtered and washed with ethyl acetate. 0.1 g of p-toluenesulfonic acid was added to the resulting solution of a mixture formed by (IIe) and (IId) in approximately 50% each and stirred for at least 30 minutes. 0.1 ml of triethylamine were added and the solvent was evaporated to dryness to obtain 0.74 g of drospirenone (I). Yield: 86%.

The invention claimed is:

1. A compound of formula (III):

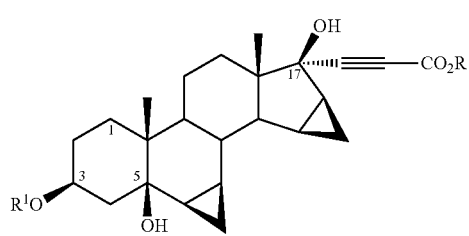

(III)

wherein
R is $C_1$-$C_8$ alkyl, $C_3$-$C_8$ cycloalkyl, aryl or benzyl; and
$R^1$ is hydrogen or a hydroxyl-protecting group;
or a solvate thereof.

2. The compound according to claim 1, selected from:
a compound of formula (III) wherein $R^1$ is hydrogen or a silylated hydroxyl-protecting group selected from trimethylsilyl and tert-butyldimethylsilyl,
a compound of formula (III) wherein R is linear or branched $C_1$-$C_8$ alkyl, and
a compound of formula (III) wherein R is linear or branched $C_1$-$C_8$ alkyl and $R^1$ is hydrogen or a silylated hydroxyl-protecting group selected from the group consisting of trimethyl-silyl and tert-butyldimethylsilyl.

3. The compound according to claim 1, selected from:

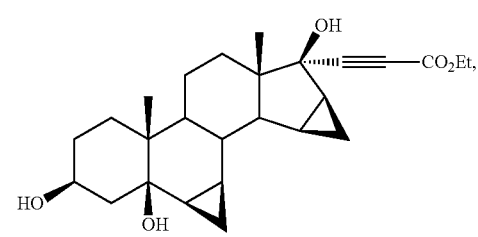

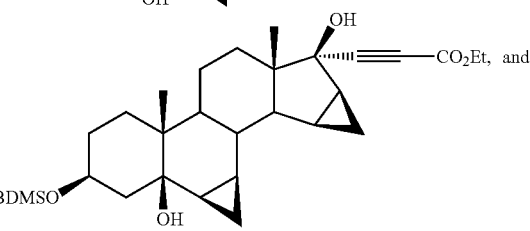

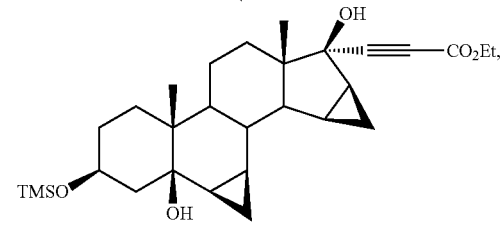

or a solvate thereof.

4. A process for obtaining a compound of formula (III)

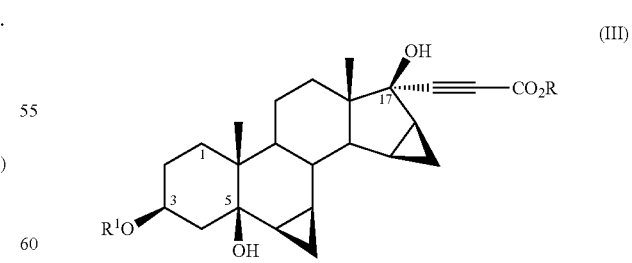

(III)

wherein
R is $C_1$-$C_8$ alkyl, $C_3$-$C_8$ cycloalkyl, aryl or benzyl; and
$R^1$ is hydrogen or a hydroxyl-protecting group;
or a solvate thereof, which comprises reacting a compound of formula (IV)

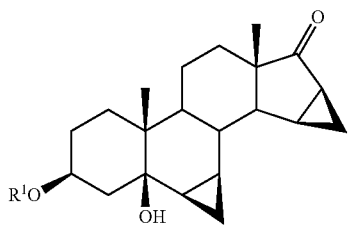

wherein $R^1$ is that previously defined,
with a propargyl ester of formula (V)

$$H{\equiv}CO_2R \qquad (V)$$

wherein R is that previously defined,
in the presence of a base.

5. The process according to claim 4, wherein the base is selected from the group consisting of lithium diethylamide, lithium diisopropylamide, lithium hexamethyldisilazide, lithium amide, sodium amide, lithium hydride, sodium hydride and mixtures thereof.

6. The process according to claim 4, wherein the reaction of the compound of formula (IV) and the compound of formula (V) is carried out in the presence of an organic solvent selected from the group consisting of diethyl ether, diisopropyl ether, tetrahydrofuran, dioxane, dichloromethane and toluene.

7. A process for obtaining Drospirenone (I)

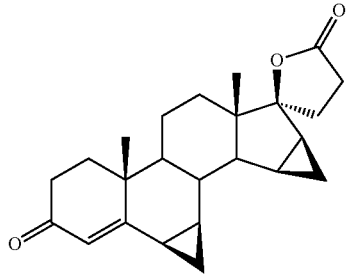

which comprises
providing a compound of formula (III)

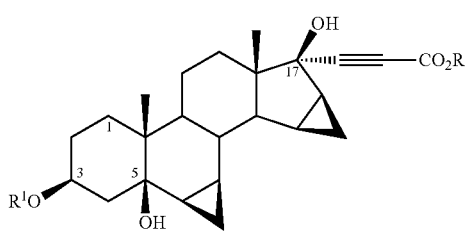

wherein
R is selected from the group consisting of $C_1$-$C_8$ alkyl, $C_3$-$C_8$ cycloalkyl, aryl and benzyl; and
$R^1$ is selected from the group consisting of hydrogen and a hydroxyl-protecting group;
or a solvate thereof, and subjecting said compound of formula (III) to:
1) optionally, deprotection of the hydroxyl group in position 3 when $R^1$ is a protecting group, and
2) oxidation of the hydroxyl group in position 3 to render a compound of formula (II)

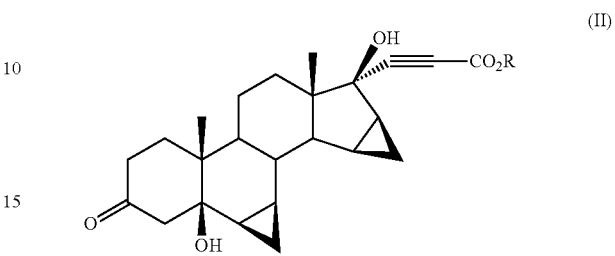

wherein R is that previously defined, and
subjecting said compound of formula (II) to a sequence of reactions selected from sequences A, B and C, wherein
Sequence A comprises:
a1) subjecting a compound of formula (II) to an elimination or an elimination/saponification reaction to yield the intermediate of formula (IIa):

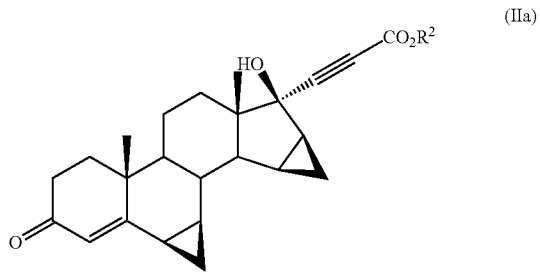

wherein $R^2$ is H, $C_1$-$C_8$ alkyl, $C_1$-$C_8$ cycloalkyl, aryl or benzyl;
a2) subjecting said compound of formula (IIa) to a hydrogenation reaction in the presence of a Pt or Pd catalyst to yield the intermediate of formula (IIc):

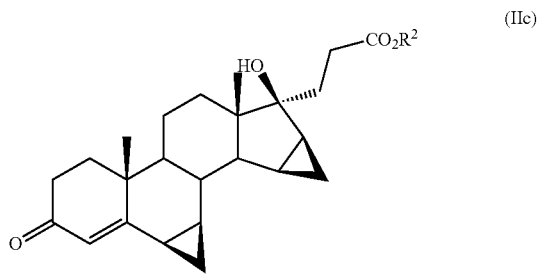

wherein $R^2$ is that previously defined, and
a3) subjecting said compound of formula (IIc) to treatment in acid conditions to render Drospirenone (I),
wherein steps a2) and a3), alternatively, take place in one-pot form;
Sequence B comprises:
b1) subjecting a compound of formula (II) to a hydrogenation reaction in the presence of a Pd catalyst to yield the intermediate of formula (IIb)

(IIb)

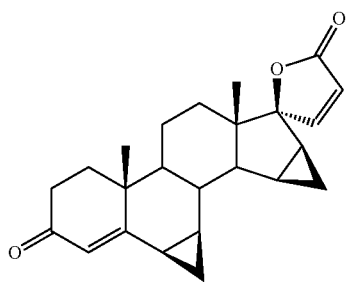

and b2) subjecting said compound of formula (IIb) to a hydrogenation reaction in the presence of a Pt catalyst to render Drospirenone (I);

wherein steps b1) and b2) alternatively take place in one-pot form; and

Sequence C comprises:

c1) subjecting a compound of formula (II) to a hydrogenation reaction in the presence of a Pt catalyst to yield the intermediates of formulae (IId) and/or (IIe)

(IIe)

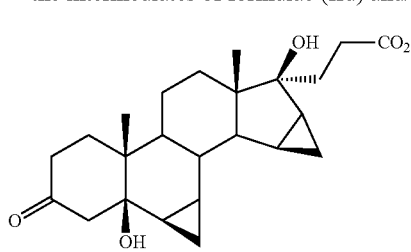

(IId)

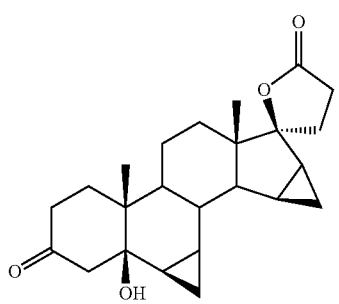

wherein R is that previously defined, and c2) subjecting a compound of formulae (IId) and/or (IIe) to treatment in acid conditions to render Drospirenone (I), wherein steps c1) and c2) alternatively take place in one-pot form;

or alternatively, a) protecting a compound of formula (IVa)

(IVa)

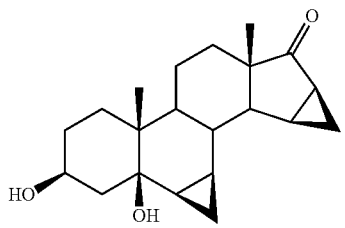

to render a compound of formula (IVb)

(IVb)

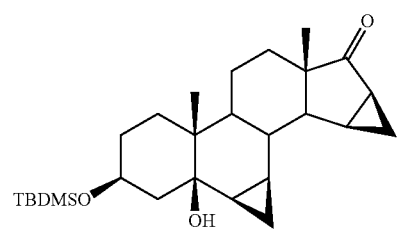

wherein TBDMS is tert-butyldimethylsilyl;

b) reacting said compound of formula (IVb) with a compound of formula (Va)

H≡CO$_2$Et  (Va)

to render a compound of formula (IIIb)

(IIIb)

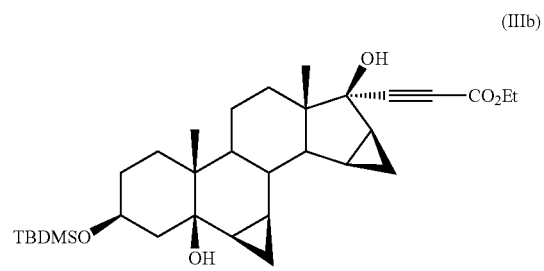 [SMILES: CCOC(=O)C#C[C@]1(O)[C@H]2C[C@H]2C2C3C(CC[C@@]21C)[C@@]1(C)CC[C@H](O[Si](C)(C)C(C)(C)C)C[C@@]1(O)[C@@H]1C[C@H]31]

wherein TBDMS is tert-butyldimethylsilyl;

c) deprotecting the protected hydroxyl group in position 3 of said compound of formula (IIIb) to render a compound of formula (IIIc)

(IIIc)

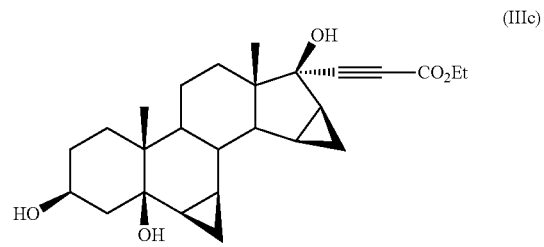 [SMILES: CCOC(=O)C#C[C@]1(O)[C@H]2C[C@H]2C2C3C(CC[C@@]21C)[C@@]1(C)CC[C@H](O)C[C@@]1(O)[C@@H]1C[C@H]31]

d) oxidizing the hydroxyl group in position 3 of said compound of formula (IIIc) in the presence of an oxidizing reagent to yield a compound of formula (IIf)

(IIf)

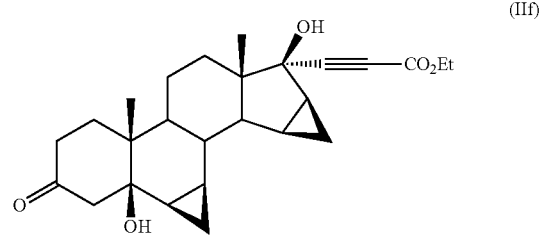

e) subjecting the compound of formula (IIf) to an elimination reaction to yield the intermediate of formula (IIg)

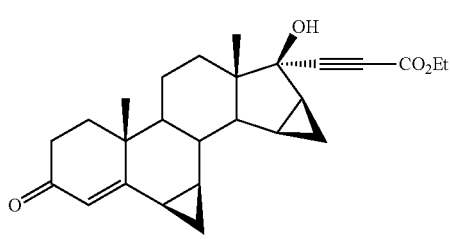

(IIg)

f) subjecting the compound of formula (IIg) to a hydrogenation reaction in the presence of a Pt catalyst to yield the intermediate of formula (IIh)

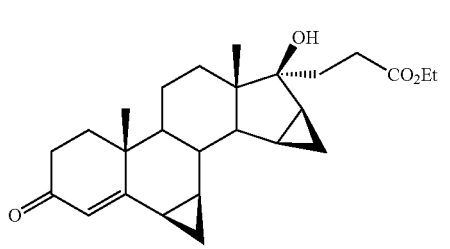

(IIh)

and g) subjecting the compound of formula (IIh) to treatment in the presence of an acid to render Drospirenone (I);

or alternatively, a') protecting a compound of formula (IVa)

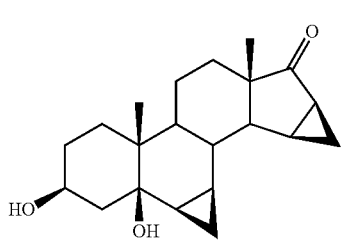

(IVa)

to render a compound of formula (IVb)

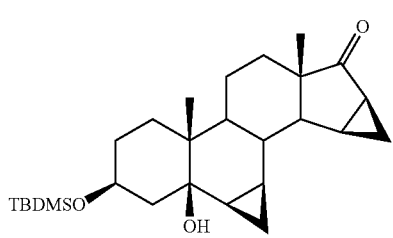

(IVb)

wherein TBDMS is tert-butyldimethylsilyl;

b') reacting a compound of formula (IVb) with a compound of formula (Va)

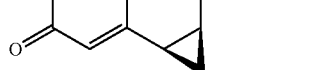

(Va)

to render a compound of formula (IIIb)

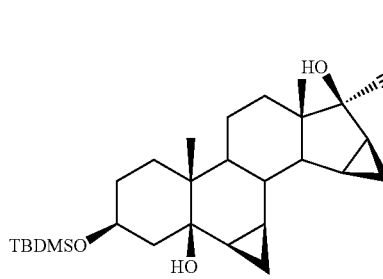

(IIIb)

wherein TBDMS is tert-butyldimethylsilyl;

c') deprotecting the protected hydroxyl group in position 3 of said compound of formula (IIIb) to render a compound of formula (IIIc)

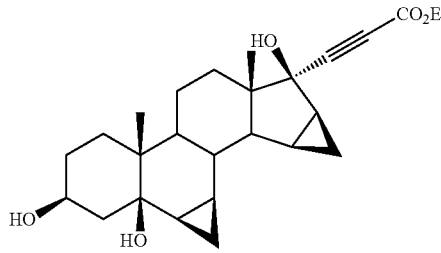

(IIIc)

d') oxidizing the hydroxyl group in position 3 of said compound of formula (IIIc) in the presence of an oxidizing reagent to yield a compound of formula (IIf)

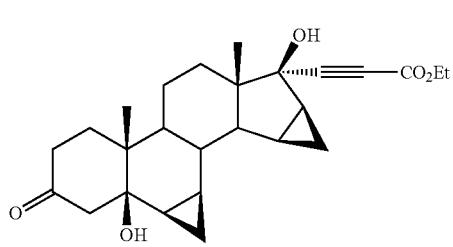

(IIf)

e') subjecting the compound of formula (IIf) to an elimination and saponification reaction to yield the intermediate of formula (IIi)

(IIi)

f') subjecting the compound of formula (IIi) to a hydrogenation reaction in the presence of a Pt or Pd catalyst to yield the intermediate of formula (IIj)

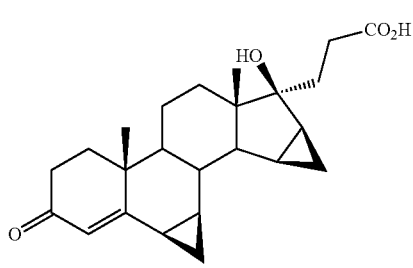

(IIj)

and g') subjecting the compound of formula (IIj) to treatment in the presence of an acid to render Drospirenone (I);

or alternatively providing a compound of formula (III)

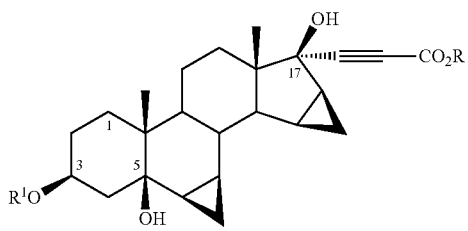

(III)

wherein

R is $C_1$-$C_8$ alkyl, $C_3$-$C_8$ cycloalkyl, aryl or benzyl; and $R^1$ is hydrogen or a hydroxyl-protecting group;

or a solvate thereof, followed by d1) subjecting said compound of formula (III) to a hydrogenation reaction in the presence of a metal catalyst to yield the intermediate of formula (VI)

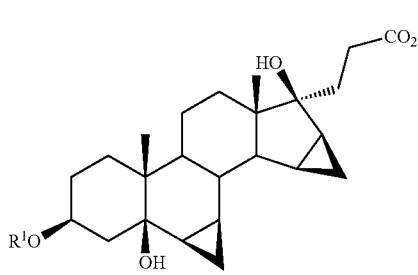

(VI)

wherein R is that previously defined, d2) deprotecting the hydroxyl group in position 3 of said compound of formula (VI) when $R^1$ is a protecting group, followed by a transesterification reaction to render the compound of formula (VII)

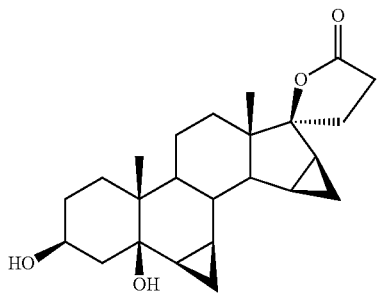

(VII)

d3) oxidizing the compound of formula (VII) to render the compound of formula (IId)

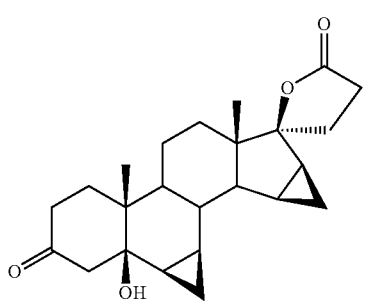

(IId)

and d4) subjecting the compound of formula (IId) to an elimination reaction to render Drospirenone (I).

8. The process according to claim 7, wherein the hydroxyl group deprotection step is carried out in the presence of a fluoride salt.

9. The process according to claim 7, wherein the oxidation step is carried out in the presence of an oxidizing reagent.

10. The process according to claim 7, wherein the elimination reaction is carried out in the presence of para-toluene-sulfonic acid or potassium bisulfate or sodium carbonate, wherein the elimination and saponification reaction is carried out in the presence of lithium hydroxide.

11. The process according to claim 7, wherein the treatment step under acid conditions is carried out using para-toluenesulfonic acid or potassium bisulfate.

12. The process according to claim 7, wherein the Pd catalyst is Pd/C and the Pt catalyst is Pt/C.

13. A compound selected from the group consisting of:

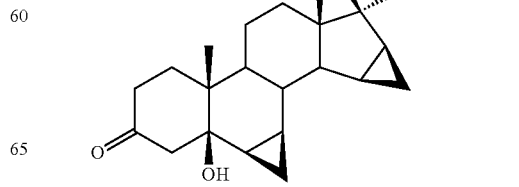

-continued
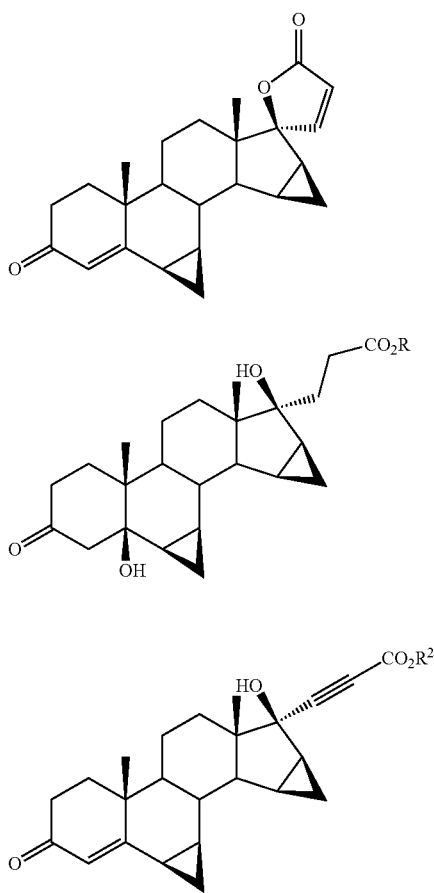
wherein
R is $C_1$-$C_8$ alkyl, $C_3$-$C_8$ cycloalkyl, aryl or benzyl; and
$R^2$ is $C_1$-$C_8$ alkyl, $C_3$-$C_8$ cycloalkyl, aryl or benzyl;
or a solvate thereof.
14. The compound according to claim 13, selected from the group consisting of:
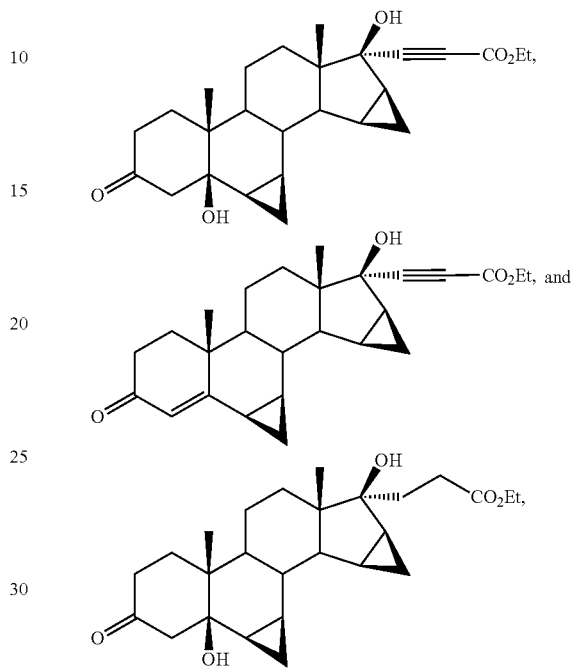
or a solvate thereof.
* * * * *